United States Patent
Guo et al.

(10) Patent No.: US 7,662,628 B2
(45) Date of Patent: Feb. 16, 2010

(54) HUMAN AKT3 NUCLEIC ACID AND USES THEREOF

(75) Inventors: Kun Guo, Eagleville, PA (US); Kenneth L. Clark, Linton (GB); Yuri D. Ivashchenko, Hattersheim (DE); Marco Pagnoni, Norristown, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 377 days.

(21) Appl. No.: 11/063,691

(22) Filed: Feb. 23, 2005

(65) Prior Publication Data

US 2005/0142603 A1 Jun. 30, 2005

Related U.S. Application Data

(62) Division of application No. 09/526,043, filed on Mar. 14, 2000, now Pat. No. 6,881,555.

(60) Provisional application No. 60/125,108, filed on Mar. 19, 1999.

(51) Int. Cl.
   *C12N 15/09* (2006.01)
   *C12Q 1/70* (2006.01)
(52) U.S. Cl. .......................... 435/455; 435/5
(58) Field of Classification Search ..................... 514/44
   See application file for complete search history.

(56) References Cited

U.S. PATENT DOCUMENTS

| 5,958,773 | A | 9/1999 | Monia et al. |
| 5,985,635 | A | 11/1999 | Bandman et al. |
| 6,043,090 | A | 3/2000 | Monia et al. |
| 6,054,285 | A | 4/2000 | Hemmings et al. |
| 7,368,420 | B1 * | 5/2008 | Walsh ........................... 514/2 |

FOREIGN PATENT DOCUMENTS

| JP | 8109197 | 4/1994 |
| WO | WO 97/18303 | 5/1997 |
| WO | WO 00/37613 | 6/2000 |
| WO | WO 00/56866 | 9/2000 |
| WO | WO 00/58473 | 10/2000 |
| WO | WO 00/77190 | 12/2000 |

OTHER PUBLICATIONS

Yia-Herttuala et al, (The Lancet, 355: 213-22, 2000.*
Hajjar et al, (Circ Res, 86: 616-621, 2000.*
O'Neil et al, (The Journal of Clinical Investigation, 115(8): 2059-2064, 2005.*
Manning et al, (Cell, 129: 1261-1274, 2007.*
Mullonkal et al, (Journal of Investigative Surgery, 20(3): 195-203, 2007.*
Ecke et al , Goodman & Gilman's The Pharmacological basis of Therapeutics, McGraw-Hill, New York, NY. pp. 77-101.*
Franke et al, Oncogene, 22: 8983-8998, 2003.*
Matsui et al (Journal of Molecular and Cellular Cardiology, 38: 63-71, 2005.*
Ichijo et al, (Science, 275: 990-94, 1997.*
Brodbeck et al (JBC, 274(14): 9133-9136, 1999.*
Okubo et al, (JBC, 273(40): 25961-25966, 1998.*
Downward et al, (Current Opinion in Cell Biology, 10: 262-267, 1998.*
Andrea Kauffmann-Zeh et al., Suppression of c-Myc-induced Apoptosis by Ras Signalling Through PI(3)K and PKB, Nature, vol. 3856, Feb. 6, 1997, pp. 544-548.
Anke Klippel et al., A Specific Product of Phosphatidylinositol 3-Kinase Directly Activates the Protein Kinase Akt through its Pleckstrin Homology Domain, Molecular and Cellular Biology, Jan. 1997, pp. 338-344.
Brian A. Hemmings, Akt Signaling: Linking Membrane Events to Life and Death Decisions, Science, vol. 275, Jan. 31, 1997, pp. 628-630.
Brian A. Hemmings, PtdIns(3,4,5)P3 Gets Its Message Across, Science, vol. 277, Jul. 25, 1997, p. 534.
Darren A.E. Cross et al., Inhibition of Glycogen Synthase Kinase-3 by Insulin Mediated by Protein Kinase B, Nature, vol. 378, Dec. 1995, pp. 785-789.
Darui R. Alessi et al., Mechanism of Activation of Protein Kinase B by insulin and IGF-1, EMBO Journal, vol. 5, pp. 6541-6551.
David Stokoe et al., Dual Role of Phosphatidylinositol-3,4,5-triphosphate in the Activation of Protein Kinase B, Science, vol. 277, Jul. 25, 1997, pp. 567-570.
George Kulik et al., Antiapoptotic Signalling by the Insulin-Like Growth Factor I Receptor, Phosphatidylinositol 3-Kinase, and Akt, Molecular and Cellular Biology, Mar. 1997, pp. 1595-1606.
Henryk Dudek et al., Regulation of Neuronal Survival by the Serine-Threonine Protein Kinase Akt, Science, vol. 275, Jan. 31, 1997, pp. 661-665.
Hidenori Ichijo et al., Induction of Apoptosis by ASK1, a Mammalian MAPKKK That Activates SAPK/JNK and p38 Signaling Pathways, Science, vol. 275, Jan. 3, 1997, pp. 90-94.
Hiroaki Konishi et al., Molecular Cloning and Characterization Of A New Member Of The RAC Protein Kinase amily: Association of the Pleckstrin Homology Domain of Three Types of RAC Protein Kinase With Protein Kinase C Subspecies and Betay Subunits of G Proteins, Biochem. & Biophysical Research Comm. vol. 216, No. 2, Nov. 13, 1995, pp. 526-534.
Howard Y. Chang et al., Activation of Apoptosis Signal-Regulating Kinase 1 (ASK1) by the Adapter Protein Daxx, Science, vol. 281, Sep. 18, 1998, pp. 1860-1862.
Jerry M. Adams et al, The Bcl-2 Protein Family: Arbiters of Cell Survival, Science, vol. 281, Aug. 28, 1998, pp. 1322-1326.
Poustka et al., Database EMBL Nucleotide and Protein Sequences, Sep. 15, 1999, Abstract XP002153016.
Len Stephens et al., Protein Kinase B Kinases That Mediate Phosphatidylinositol 3,4,5-Trisphosphate-Dependent Activation of Protein Kinase B, Science, vol. 279, Jan. 30, 1998, pp. 710-714.

(Continued)

*Primary Examiner*—Anne-Marie Falk
*Assistant Examiner*—Magdalene K Sgagias

(57) ABSTRACT

The present invention relates to human Akt3 proteins and polypeptides. The invention also relates to isolated nucleic acids encoding human Akt3, to vectors containing them and to their therapeutic uses, in particular for gene therapy. Expression of Akt3 inhibits cell death associated with hypoxia, apoptosis or necrosis.

8 Claims, 7 Drawing Sheets

OTHER PUBLICATIONS

M. Barinaga, Is Apoptosis Key in Alzheimer's Disease?, Science, vol. 281, Aug. 28, 1998, pp. 1303-1304.

M. Barinaga, Stroke-Damaged Neurons May Commit Cellular Suicide, Science, vol. 281, Aug. 28, 1998, pp. 1302-1303.

Nancy A. Thornberry et al., Caspases: Enemies Within, Science, vol. 281, Aug. 28, 1998, pp. 1312-1316.

Nicholas Pullen at al., Phosphorylation and Activation of p70s6k by PDK1, Science, vol. 279, Jan. 30, 1998.

Thomas F. Franke et al., Direct Regulation of the Akt Proto-Oncogene Product by Phosphatidylinositoi-3,4-bisphosphate, Science, vol. 275, Jan. 31, 1997, pp. 665-668.

Thomas F. Franke et al., The Protein Kinase Encoded by the Akt Proto-Oncogene Is a Target of the PDFG-Activated Phosphatidylinositol 3-Kinase, Cell, vol. 81. Issue 5, Jun. 2, 1995, pp. 727-736.

W. Robb MacLellan et al., Death by Design, Programme Cell Death in Cardiovascular Biology and Disease, Circulation Research, vol. 81, 1997, pp. 137-144.

Yumiko Okubo et al., insulin-like Growth Factor-I Inhibits the Stress-activated Protein Kinase/c-Jun N-terminal Kinase, Journ. of Biological Chem., vol. 273, No. 40, Oct. 2, 1998, pp. 25951-25966.

Brodbeck et al., A Human Protein Kinase By with Regulatory Phosphorylation Sites in Activation Loop and in the C-terminal Hydrophobic Domain, Journ. of Biological Chem., vol. 274, No. 14, Apr. 2, 1999, pp. 9133-9136.

Walker et al., Activation of Protein Kinase B Beta and y isoforms by Insulin in vivo and by 3-phosphoinositide-dependent protein kinase-1 in vito: Comparison With Protein Kinase B alpha, Biochem, Journal, vol. 331, 1998, pp. 299-308.

Nakatani et al., Identification of a Human Akt3 (Protein Kinase B y) Which Contains the Regulatory Serine Phosphorylation Site, Biochem. and Biophys. Res. Comm. vol. 257, 1999, pp. 906-910.

Matsui et al. Adenoviral Gene Transfer of Activated Phosphatidylinositol 3'-Kinase and Akt Inhibits Apoptosis of Hypoxic Cardiomyocytes In Vitro, U.S. American Heart Association, vol. 100, No. 23, Dec. 7,1999, pp. 2373-2379.

J. Downward, Mechanisms and Consequences Of Activation of Protein Kinase B/Akt, Curr Opin. Cell Biol. vol. 10, No. 2, 1998, pp. 262-267.

Franke et al., P13K: Downstream AKTion Blocks Apoptosis, Cell, vol. 88, Feb. 21, 1997, pp. 435-437.

S. Staal, Molecular Cloning of the akt Oncogene and Its Human Homologues AKT1 and AKT2: Amplification of AKT1 in a Primary Human Gastric Adenocarcinoma, Proc., Natl, Acad, Sci, USA, vol. 84, Jul. 1987, pp. 5034-5037.

Konishi et al, Molecular Cloning and characterization of a new member of the RAC protein kinase family Association of the pleckstrin homology domain of the three types of RAC protein kinase with protein kinase C subspecies and beta alpha subunits of G, 1995.

Amino acid and nucleic acid databases, Accession No. D49386, 1999.

Cargill et al, Characterization of single-nucleotide polymorphisms in coding regions of human genes Nature Genetics, Jul. 1999, vol. 22, pp. 231-238.

Cargill et al, Characterization of single-nucleotide polymorphisms in coding regions of human genes Nature Gentics, Nov. 1999, vol. 23, p. 373.

Kennedy et al., The PI 3-kinase/Akt signaling pathway delivers an anti-apoptotic signalGenes and Development, Feb. 1997, vol. 11, pp. 701-713.

Liu et al., Constitutively Activated Akt-1 Is Vital for the Survival of Human Monocyte-diffrentiated Macrophages, J. Exp. Med., Jul. 2001, vol. 194, pp. 113-126.

Altschul et al., Gapped BLAST and PSI-BLAST: a new generation of protein database search programsNucleic Acids Research, 1997, vol. 25, pp. 3389-3402.

Walker et al., Activation of protein kinase B g and n isoforms by insulin in vivo and by 3-phosphoinositide-dependent protein kinase-1 in vitro: comparison with protein kinase B f Biochemical Journal, 1998, vol. 331, pp. 299-308.

Wang et al., Regulation of Cardiomyocyte Apoptotic Signaling by Insulin-like Growth Factor I, Circ. Res., Jun. 1998, vol. 83, pp. 516-522.

Konishi et al., Molecular Cloning and Characterization of a New Member of the RAC Protein Kinase Family: Association of the Pleckstrin Homology Domain of 3 Types of RAC Protein Kinase with Protein Kinase C Subspecies and βγSubunits of G Proteins Biochem & Biophys Res. comm Nov. 1995; vol. 216, pp. 526-534.

Pugazhenthi et al., Akt/Protein Kinase B Up-regulates Bcl-2 Expression through camp response Element-binding Protein, J. Bio. Chem., Apr. 2000, vol. 275, pp. 10761-10766.

Masurs et al., Molecular cloning, expression and characterization of the human serine/threonine kinase Akt-3, Eur. J. Biochem., Feb. 1999, vol. 265, pp. 353-360.

Andersson et al., a double adaptor method for improved shotgun library construction, Anal. Biochem. 1996, vol. 236, No. 1, pp. 107-113.

Bonaldo et al., Normalization and subtraction: two approaches to facilitate gene discovery, Genome Research, 1996, vol. 6, No. 9., pp. 791-806.

Hillier, et al, Generation and analysis of 280,000 human expressed sequence tags, Genome Research, 1996, vol. 8, No. 9., pp. 807-828.

Hillier et al., The WashU-Merck EST Project. Accession No. N51277, created Feb. 18, 1996, updated Mar. 4, 2000.

Hillier et al., the WashU-Merck EST Project, Accession No. H09074, created Jul. 2, 1995. updated Mar. 4, 2000.

Hillier et al. The WashU-Merck human EST Project, Accession No. AA161465; created Jan. 19, 1997, updated Mar. 3, 2000.

National Cancer Institute, Cancer Genome Anatomy Project (CGAP, Tumor Gene Index, http://www/ncbi.nlm.nih.gov/ncigap: Accession No. AW193663, created Nov. 30, 1999, updated Mar. 4, 2000.

National Cancer Institute, Cancer Genome Anatomy Project (CGAP, Tumor Gene Index, http://www/ncbi.nlm.nih.gov/ncigap; Accession No. AI089322, created Aug. 19, 1998, updated Mar. 3, 2000.

\* cited by examiner

Figure 1A

```
              1                                                              50
h-akt3    MSDVTIVKEG WVQKRGEYIK NWRPRYFLLK TDGSFIGYKE KPQDVDLPYP
rat-akt3  MSDVTIVKED WVQKRGEYIK NWRPRYFLLK TDGSFIGYKE KPQDVDLPYP 51                                                             100
h-akt3    LNNFSVAKCQ LMKTERPKPN TFIIRCLQWT TVIERTFHVD TPEEREEWTE
rat-akt3  LNNFSVAKCQ LMKTERPKPN TFIIRCLQWT TVIERTFHVD TPEEREEWTE 101                                                            150
h-akt3    AIQAVADRLQ RQEEERMNCS PTSQIDNIGE EEMDASTTHH KRKTMNDFDY
rat-akt3  AIQAVADRLQ RQEEERMNCS PTSQIDNIGE EEMDASTTHH KRKTMNDFDY 151                                                            200
h-akt3    LKLLGKGTFG KVILVREKAS GKYYAMKILK KEVIIAKDEV AHTLTESRVL
rat-akt3  LKLLGKGTFG KVILVREKAS GKYYAMKILK KEVIIAKDEV AHTLTESRVL 201                                                            250
h-akt3    KNTRHPFLTS LKYSFQTKDR LCFVMEYVNG GELFFHLSRE RVFSEDRTRF
rat-akt3  KNTRHPFLTS LKYSFQTKDR LCFVMEYVNG GELFFHLSRE RVFSEDRTRF 251                                                            300
h-akt3    YGAEIVSALD YLHSGKIVYR DLKLENLMLD KDGHIKITDF GLCKEGITDA
rat-akt3  YGAEIVSALD YLHSGKIVYR DLKLENLMLD KDGHIKITDF GLCKEGITDA 301                                                            350
h-akt3    ATMKTFCGTP EYLAPEVLED NDYGRAVDWW GLGVVMYEMM CGRLPFYNQD
rat-akt3  ATMKTFCGTP EYLAPEVLED NDYGRAVDWW GLGVVMYEMM CGRLPFYNQD 351                                                            400
h-akt3    HEKLFELILM EDIKFPRTLS SDAKSLLSGL LIKDPNKRLG GGPDDAKEIM
rat-akt3  HEKLFELILM EDIKFPRTLS SDAKSLLSGL LIKDPNKRLG GGPDDPKEIM 401                                                            450
h-akt3    RHSFFSGVNW QDVYDKKLVP PFKPQVTSET DTRYFDEEFT AQTITITPPE
rat-akt3  RHSFFSGVNW QDVYDKKLVP PFKPQVTSET DTRYFDEEFT AQTITITPPE 451        465
h-akt3    KCQQSDCGML GNWKK
rat-akt3  KCPL
```

Figure 1B

```
            1                                                      50
h-akt1    MSDVAIVKEG  WLHKRGEYIK  TWRPRYFLLK  NDGTFIGYKE  RPQDVDQREA
h-akt2    MNEVSVIKEG  WLHKRGEYIK  TWRPRYFLLK  SDGSFIGYKE  RPEAPDQTLP
h-akt3    MSDVTIVKEG  WVQKRGEYIK  NWRPRYFLLK  TDGSFIGYKE  KPQDVDLPY- 51                                                     100
h-akt1    PLNNFSVAQC  QLMKTERPRP  NTFIIRCLQW  TTVIERTFHV  ETPEEREEWT
h-akt2    PLNNFSVAEC  QLMKTERPRP  NTFVIRCLQW  TTVIERTFHV  DSPDEREEWM
h-akt3    PLNNFSVAKC  QLMKTERPKP  NTFIIRCLQW  TTVIERTFHV  DTPEEREEWT 101                                                    150
h-akt1    TAIQTVADGL  RKQE--EEEM  DFRSGSPSDN  SGAEEMEVSL  AKPKHRVTMN
h-akt2    RAIQMVANSL  KQRAPGEDPM  DYKCGSPSDS  STTEEMEVAV  SKARAKVTMN
h-akt3    EAIQAVADRL  QRQE--EERM  NCSPTSQIDN  IGEEEMDAST  THHKRK-TMN 151                                                    200
h-akt1    EFEYLKLLGK  GTFGKVILVK  EKATGRYYAM  KILKKEVIVA  KDEVAHTLTE
h-akt2    DFDYLKLLGK  GTFGKVILVR  EKATGRYYAM  KILRKEVIIA  KDEVAHTVTE
h-akt3    DFDYLKLLGK  GTFGKVILVR  EKASGKYYAM  KILKKEVIIA  KDEVAHTLTE 201                                                    250
h-akt1    NRVLQNSRHP  FLTALKYSFQ  THDRLCFVME  YANGGELFFH  LSRERVFSED
h-akt2    SRVLQNTRHP  FLTALKYAFQ  THDRLCFVME  YANGGELFFH  LSRERVFTEE
h-akt3    SRVLKNTRHP  FLTSLKYSFQ  TKDRLCFVME  YVNGGELFFH  LSRERVFSED 251                                                    300
h-akt1    RARFYGAEIV  SALDYLHSEK  NVVYRDLKLE  NLMLDKDGHI  KITDFGLCKE
h-akt2    RARFYGAEIV  SALEYLHS-R  DVVYRDIKLE  NLMLDKDGHI  KITDFGLCKE
h-akt3    RTRFYGAEIV  SALDYLHSGK  -IVYRDLKLE  NLMLDKDGHI  KITDFGLCKE 301                                                    350
h-akt1    GIKDGATMKT  FCGTPEYLAP  EVLEDNDYGR  AVDWWGLGVV  MYEMMCGRLP
h-akt2    GISDGATMKT  FCGTPEYLAP  EVLEDNDYGR  AVDWWGLGVV  MYEMMCGRLP
h-akt3    GITDAATMKT  FCGTPEYLAP  EVLEDNDYGR  AVDWWGLGVV  MYEMMCGRLP 351                                                    400
h-akt1    FYNQDHEKLF  ELILMEEIRF  PRTLGPEAKS  LLSGLLKKDP  KQRLGGGSED
h-akt2    FYNQDHERLF  ELILMEEIRF  PRTLSPEAKS  LLAGLLKKDP  KQRLGGGPSD
h-akt3    FYNQDHEKLF  ELILMEDIKF  PRTLSSDAKS  LLSGLLIKDP  NKRLGGGPDD 401                                                    450
h-akt1    AKEIMQHRFF  AGIVWQHVYE  KKLSPPFKPQ  VTSETDTRYF  DEEFTAQMIT
h-akt2    AKEVMEHRFF  LSINWQDVVQ  KKLLPPFKPQ  VTSEVDTRYF  DDEFTAQSIT
h-akt3    AKEIMRHSFF  SGVNWQDVYD  KKLVPPFKPQ  VTSETDTRYF  DEEFTAQTIT 451              482
h-akt1    ITPPDQDDSM  ECVDSERRPH  FPQFSYSASS  TA
h-akt2    ITPPDRYDSL  GLLELDQRTH  FPQFSYSASI  R
h-akt3    ITPPEKCQQS  DCGMLGNWKK
```

HUMAN AKT3 NUCLEIC ACID AND USES THEREOF

CROSS REFERENCE TO RELATED APPLICATIONS

This application is a divisional of U.S. patent application Ser. No. 09/526,043 filed on Mar. 14, 2000, issued as U.S. Pat. No. 6,881,555 on Apr. 19, 2005, which claims the benefit of U.S. Provisional Application No. 60/125,108, filed on Mar. 19, 1999, which are hereby incorporated by reference herein in their entireties.

FIELD OF THE INVENTION

The present invention relates to isolated nucleic acids, to vectors containing them and to their therapeutic uses, in particular in gene therapy. More especially, the present invention relates to nucleic acids encoding an Akt isoform, designated Akt3, and to their use in gene therapy. Expression of activated Akt3 prevents apoptotic cell death induced by apoptosis stimulating kinase 1 (ASK1).

BACKGROUND OF THE INVENTION

Akt and Apoptosis

Apoptosis (programmed cell death) plays essential roles in embryonic development and pathogenesis of various diseases, such as degenerative neuronal diseases and cardiovascular diseases (MacLellan et al. 1998, Barinaga 1997a, Baringaga 1997b). Therefore, recent work has led to the identification of various pro- and anti-apoptotic gene products that are involved in the regulation or execution of programmed cell death. Expression of anti-apoptotic genes, such as Bcl2 or Bcl-x, inhibits apoptotic cell death induced by various stimuli. On the other hand, expression of pro-apoptotic genes, such as Bax or Bad, leads to programmed cell death (Aams et al. 1998). The execution of programmed cell death is mediated by caspase-1 related proteinases, including caspase-1, caspase-3, caspase-7, caspase-8 and caspase-9 etc (Thorneberry et al. 1998).

Recently, two intracellular signaling pathways involved in the regulation of cell survival/death have been studied. Activation of apoptotic stimulating kinase1 (ASK1) leads to apoptosis in various cell types (Ichijo et al. 1997), while a pathway involving phosphoinositide 3-kinase (PI3K) and Akt leads to cytoprotection. It has been demonstrated that the activity of ASK1 is induced by tumor necrosis factor-alpha (TNFa) treatment or Fas ligation (Ichijo et al. 1997, Chang et al. 1998). Overexpression of ASK1 dominant negative mutants inhibit apoptosis induced by TNFa or Fas ligation, indicating that ASK1 plays important roles during TNFa or Fas ligation-induced apoptotic cell death. The molecular mechanism by which ASK1 induces apoptosis is not clear. It has been shown that ectopic expression of ASK1 leads to activation of various stress-activated signaling pathways, such as the MKK4/JNK and MKK6/p38 pathways, which may mediate ASK1-induced apoptosis (Ichijo et al. 1997).

The PI3K/Akt pathway also appears important for regulating cell survival/cell death (Kulik et al. Franke et al 1997, Kauffmann-Zeh et al, Hemmings 1997. Dudek et al. 1997). Survival factors, such as platelet derived growth factor (PDGF), nerve growth factor (NGF) and insulin-like growth factor-1 (IGF-1), promote cell survival under various conditions by inducing the activity of PI3K (Kulik et al. 1997, Hemmings 1997). Activated PI3K leads to the production of phosphatidylinositol (3,4,5)-triphosphate (PtdIns(3,4,5)-P3), which in turn binds to and induces the activity of a AH/PH-domain containing serine/threonine kinase, Akt (Franke et al 1995, Hemmings 1997b, Downward 1998, Alessi et al. 1996). Specific inhibitors of PI3K or dominant negative Akt mutants abolish survival-promoting activity of these growth factors or cytokines. In addition, introduction of constitutively active PI3K or Akt mutants promotes cell survival under conditions in which cells normally undergo apoptotic cell death (Kulik et al. 1997, Dudek et al. 1997). These observations demonstrate that the PI3K/Akt pathway plays important roles for regulating cell survival or apoptosis.

Two isoforms of human Akt protein kinases, Akt1 and Akt2 have been identified (Staal. 1987). A rat Akt sequence has also been identified (Konishi et al. 1995). Serine-473 in the C-terminus of human Akt1 has been shown to be critical for its regulation (Stokeo et al. 1997; Stephens et al. 1998). Upon growth factor stimulation, PI3K is activated. The product of PI3K, PtdIns(3.4.5)-P binds Akt1, and causes translocation of Akt1 from the cytoplasm to the proximity of the inner cytoplasmic membrane, where it becomes phosphorylated at residues Thr308 and Ser473 (Downward, 1998). Phosphorylation of these residues is critical for the activation of Akt1. A recently identified protein kinase, PDK1, has been shown to be responsible for the phosphorylation of Thr308, while the kinase(s) which phosphorylates Ser473 has not yet been identified (Stokeo et al. 1997, Stephens et al. 1998).

Gene Therapy

Gene therapy involves correcting a deficiency or abnormality (mutation, aberrant expression, and the like) by introduction of genetic information into a patient, such as into an affected cell or organ of the patient. This genetic information may be introduced either in vitro into a cell, the modified cell then being reintroduced into the body, or directly in vivo into an appropriate site. In this connection, different techniques of transfection and of gene transfer have been described in the literature (see Roemer and Friedman, Eur. J. Biochem. 208 (1992) 211), including transfection of "naked DNA" and various techniques involving complexes of DNA and DEAE-dextran (Pagano et al., J. Virol. 1 (1967) 891), of DNA and nuclear proteins (Kaneda et al., Science 243 (1989) 375), of DNA and lipids (Felgner et al., PNAS 84 (1987) 7413), the use of liposomes (Fraley et al., J. Biol. Chem. 255 (1980) 10431) and the like. More recently, the use of viruses as vectors for the transfer of genes has emerged as a promising alternative to physical transfection techniques. In this regard, different viruses have been tested for their capacity to infect certain cell populations, including retroviruses, herpes viruses, adeno-associated viruses, and adenoviruses.

The citation of any reference herein should not be construed as an admission that such reference is available as "Prior Art" to the instant application.

SUMMARY OF THE INVENTION

A first subject of the invention relates to an isolated nucleic acid encoding a novel Akt protein or polypeptide. More specifically, the invention relates to an isolated nucleic acid encoding a human Akt3 protein comprising the sequence Cys-Gln-Gln-Ser-Asp-Cys-Gly-Met-Leu-Gly-Asn-Trp-Lys-Lys, or a substantially similar sequence, wherein the nucleic acid has a property selected from the following:

A. it can be amplified by polymerase chain reaction (PCR) using an oligonucleotide primer pair derived from SEQ ID NO:5 and SEQ ID NO:6;

B. it hybridizes under stringent conditions with a nucleic acid comprising a nucleotide sequence as depicted in SEQ ID NO:1;
C. it encodes a polypeptide comprising an amino acid sequence selected from the group consisting of SEQ ID NO:2, splice variants thereof, and allelic variants thereof;
D. it encodes a polypeptide which specifically binds to an antibody generated against an epitope within a peptide having the sequence Cys-Gln-Gln-Ser-Asp-Cys-Gly-Met-Leu-Gly-Asn-Trp-Lys-Lys, or a substantially similar sequence.

Preferably, the nucleic acid encodes a human Akt3 protein comprising an amino acid sequence as depicted in SEQ ID NO:2. More preferably, the nucleic acid comprises the sequence depicted in SEQ ID No. 1. The nucleic acid may, optionally, comprise a sequence encoding a polypeptide tag, thereby encoding a chimeric tagged Akt3 protein. In another aspect, the nucleic acid may, optionally, comprise a sequence encoding a myristylation sequence. In a preferred embodiment, the nucleic acid comprises a region permitting expression of the Akt3 protein in mammalian cells.

The invention also relates to vectors containing a nucleic acid as described above. Preferably, the nucleic acid encoding a human Akt3 protein is operatively associated with an expression control sequence permitting expression of human Akt3 in an expression competent host cell. The expression control sequence may comprise a promoter which is functional in mammalian cells. The vector may be a plasmid DNA molecule or a viral vector. Preferred viral vectors include retrovirus, adenovirus, adeno-associated virus, herpes virus, and vaccinia virus. Therefore, the invention further relates to a replication defective recombinant virus comprising in its genome the nucleic acid encoding Akt3 as described above.

In another embodiment, the invention relates to a host cell transfected with the vector as described above. The host cell may be a bacterial cell, a yeast cell, or a mammalian cell. In still another embodiment, the invention relates to a method for producing a human Akt3 protein comprising culturing the host cell as described above in culture medium under conditions permitting expression of human Akt3, and isolating human Akt3 protein from the culture.

The invention further relates to an isolated human Akt3 protein comprising the sequence Cys-Gln-Gln-Ser-Asp-Cys-Gly-Met-Leu-Gly-Asn-Trp-Lys-Lys, or a substantially similar sequence, and having a property selected from the following:
A. it is encoded by the nucleic acid as described above;
B. it comprises an amino acid sequence as depicted in SEQ ID NO:2, splice variants thereof, or allelic variants thereof; and
C. it specifically binds to an antibody generated against an epitope within a peptide having the sequence Cys-Gln-Gln-Ser-Asp-Cys-Gly-Met-Leu-Gly-Asn-Trp-Lys-Lys, or a substantially similar sequence.

Preferably, the protein comprises an amino acid sequence as depicted in SEQ ID NO:2. The protein may, optionally, comprise a tag sequence. In still another embodiment, the protein may, optionally, comprise a myristylation sequence.

The present invention also relates to antigenic peptides and antibodies thereto. More particularly, the invention relates to antigenic peptides comprising the sequence Cys-Gln-Gln-Ser-Asp-Cys-Gly-Met-Leu-Gly-Asn-Trp-Lys-Lys, or a substantially similar sequence, and which is a fragment of human Akt3 protein, wherein the Akt3 protein has a property selected from the following:
A. it is encoded by the nucleic acid as described above;
B. it comprises an amino acid sequence as depicted in SEQ ID NO:2, splice variants thereof, or allelic variants thereof; and
C. it specifically binds to an antibody generated against an epitope within a peptide having the sequence Cys-Gln-Gln-Ser-Asp-Cys-Gly-Met-Leu-Gly-Asn-Trp-Lys-Lys, or a substantially similar sequence.

Preferably, the antigenic peptide consists essentially of the sequence Cys-Gln-Gln-Ser-Asp-Cys-Gly-Met-Leu-Gly-Asn-Trp-Lys-Lys or an antigenic fragment thereof. In another embodiment, the invention relates to an antibody which specifically binds a human Akt3 protein as described above. In a preferred embodiment, the antibody specifically recognizes an epitope within a peptide having the sequence Cys-Gln-Gln-Ser-Asp-Cys-Gly-Met-Leu-Gly-Asn-Trp-Lys-Lys. The antibody may be polyclonal or monoclonal.

The present invention also relates to a method of inhibiting apoptosis or necrosis of a cell by administering to the cell a nucleic acid as described above. Preferably, the nucleic acid is operably linked to a regulatory region. The nucleic acid may be a plasmid or a viral vector. Preferred cells include cardiac cells. More preferably, the cell is a cardiac myocyte. In a preferred embodiment, the cell is in a patient suffering from myocardial infarction or ischemia reperfusion injury. Therefore, the present invention also relates to methods of treating myocardial infarction or ischemia reperfusion injury by administering to a patient suffering therefrom a nucleic acid as described above operably linked to a regulatory region. Preferably, the nucleic acid is administered to cardiac myocytes of a patient. The nucleic acid may be in the form a plasmid in a viral vector. Preferred viral vectors include retroviruses, adenoviruses, adeno-associated viruses, vaccinia virus and HSV virus.

The invention also relates to the use of these nucleic acids or vectors for the preparation of pharmaceutical compositions intended for the surgical and/or therapeutic treatment of the human or animal body. It also relates to any pharmaceutical composition comprising a vector, in particular a viral vector, and a nucleic acid as defined above.

In still another embodiment, the present invention relates to methods of screening for molecules that stimulate or inhibit Akt3 activity in a cell by contacting an Akt3 protein with a candidate molecule and detecting Akt3 activity in the presence of the molecule. Candidate molecules may be either agonists or antagonists of Akt3. In a preferred embodiment, the Akt3 is expressed from a nucleic acid in the cell and the Akt3 activity measured is inhibition of apoptosis. Inhibition of apoptosis can be measured by the presence of a marker gene.

The present invention also relates, generally, to methods of increasing Akt3 activity in a cell by increasing the level of an Akt3 protein in the cell. In a preferred embodiment, the cell has been transfected with a vector encoding Akt3 under conditions permitting expression of the Akt3 protein. Similarly, the invention relates to methods of inhibiting Akt3 activity in a cell by decreasing the level of an Akt3 protein in the cell. The level of Akt3 protein may be decreased by introducing an Akt3 antisense nucleic acid into the cell under conditions wherein the antisense nucleic acid hybridizes under intracellular conditions to an Akt3 mRNA. The level of Akt3 protein can also be decreased by introducing a single chain Fv antibody (scFv) that specifically binds Akt3 into the cell at a level sufficient to bind to and inactivate Akt3.

BRIEF DESCRIPTION OF THE DRAWINGS

FIG. 1: Alignment of Akt3 sequences.

FIG. 1A: Alignment of human Akt1 (SEQ ID NO:14), Akt2 (SEQ ID NO: 13) and Akt3 (SEQ ID NO: 2) amino acid sequences.

FIG. 1B: Alignment of rat Akt (SEQ ID NO: 17) and human Akt3 (SEQ ID NO: 2) amino acid sequences.

An Akt3 specific probe was prepared as described in the Examples. Multiple human tissue mRNA blot (Clontech) was hybridized with Akt3 specific probe (see the Examples for details).

FIG. 3: Construction of activated Akt3 mutant.

Figure 3A:
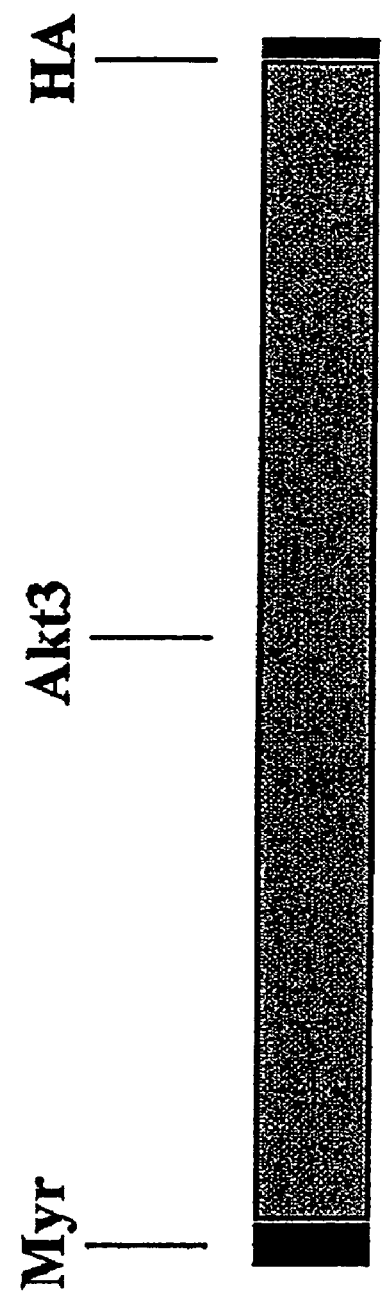

FIG. 3A: Schematic presentation of activated Akt3: Full length coding sequence of human Akt3 was fused in frame with the Myristylation signal from human Src gene (Myr) in the N-terminal, and fused in frame with the HA-tag in the C-terminus (HA). (see the Examples)

Figure 3B:
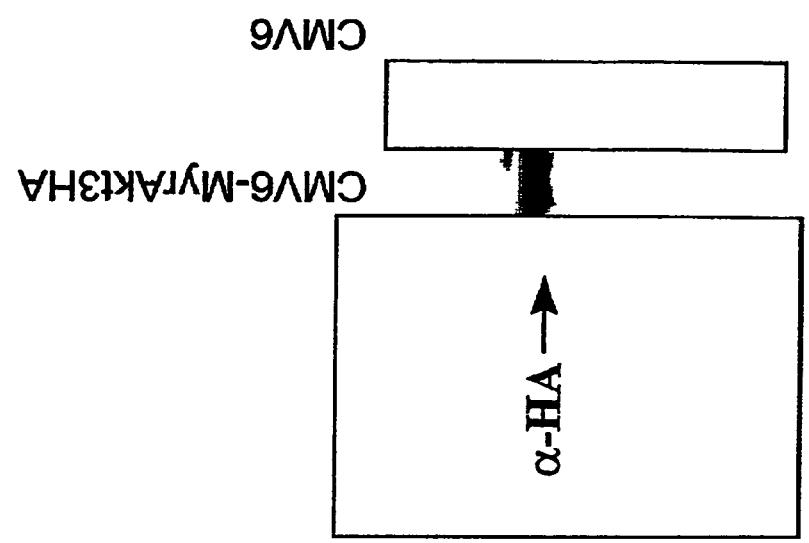

FIG. 3B: Ectopic expression of activated Akt3 in HEK293 cells. HEK293 cells were transfected with either CMV6-MyrAkt3HA or expression plasmid (CMV6) alone. 24 hours after transfections, cell lysates were prepared and subjected to immunoblotting with a-HA antibodies.

Figure 3C:
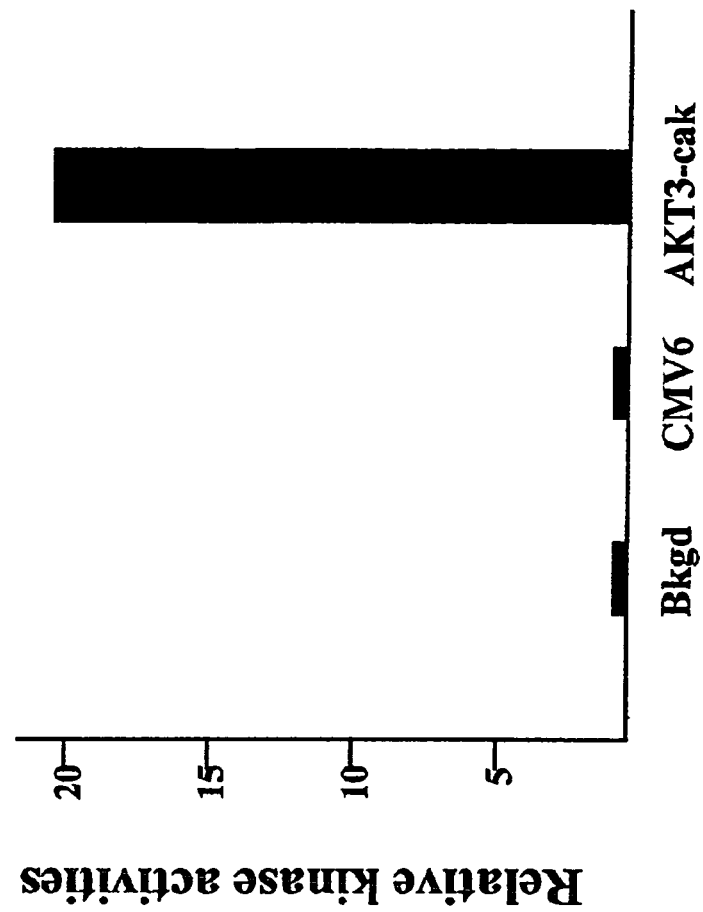

FIG. 3C: Activated Akt3 possesses Akt activity. HEK293 cells were transfected with expression plasmid for activated Akt3 (MyrAkt3HA) or expression vector alone (CMV6). 24 hours after transfections, cell lysates were prepared and subjected to immunoprecipitation with anti-HA antibodies. Akt3 kinase activities of immunopellets were measured by using substrate peptide derived from GSK3. Bkgd: background level from non-transfected cells; CMV6: CMV6 transfected cells; Akt3cak: cells transfected with expression plasmid for constitutively activated Akt3 (CMV6-MyrAkt3HA). (see the Examples).

Figure 4:
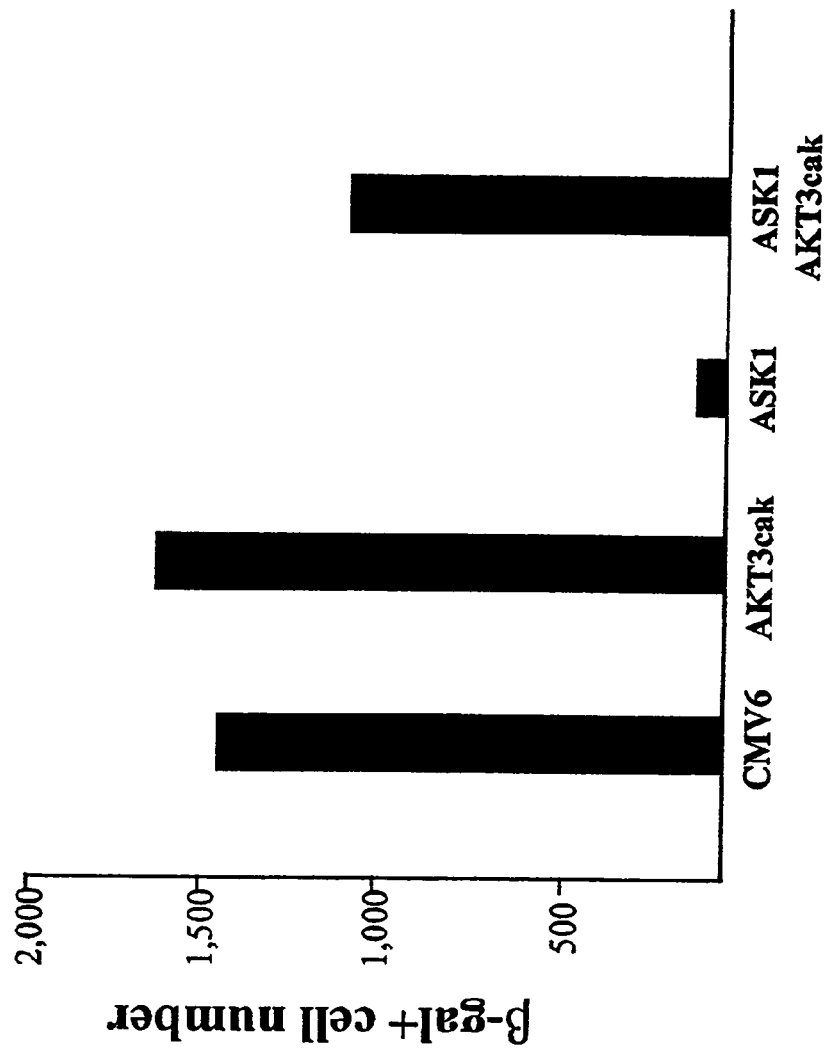

FIG. 4: Active Akt3 inhibits ASK1 induced cell death in HEK293 cells. HEK293 cells were transfected with CMV-β-gal plasmid (0.1 mg) with the combination of indicated plasmids. The amount of DNA for each transfection were kept constant by addition of CMV6 vector. Akt3cak: CMV6-MyrAkt3HA (0.4 mg); ASK1: pcDNA3HA-ASK1-fl (0.4 mg). Two days after transfections, cells were fixed and stained for X-gal staining. The number of β-gal positive cells (blue cells) were counted in five different fields under the light microscope. (See the Examples).

DETAILED DESCRIPTION OF THE INVENTION

The present invention advantageously provides an isolated nucleic acid encoding a novel Akt protein or polypeptide, designated Akt3. Therefore, a first subject of the invention relates to an isolated nucleic acid encoding a novel Akt3 protein or polypeptide under the control of regions permitting its expression in mammalian cells.

The invention also relates to vectors containing the nucleic acid encoding the Akt protein or polypeptide. The invention also relates to the use of these nucleic acids or vectors for the preparation of pharmaceutical compositions intended for the surgical and/or therapeutic treatment of the human or animal body. It also relates to any pharmaceutical composition comprising a vector, in particular a viral vector, and a nucleic acid as defined above.

The various aspects of the invention will be set forth in greater detail in the following sections, directed to the nucleic acids, vectors, viruses, compositions, and methods of treatment of the invention. This organization into various sections is intended to facilitate understanding of the invention, and is in no way intended to be limiting thereof.

Definitions

The following defined terms are used throughout the present specification, and should be helpful in understanding the scope and practice of the present invention.

In a specific embodiment, the term "about" or "approximately" means within 20%, preferably within 10%, and more preferably within 5% of a given value or range.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

A "gene" refers to an assembly of nucleotides that encode a polypeptide, and includes cDNA and genomic DNA nucleic acids.

A "recombinant DNA molecule" is a DNA molecule that has undergone a molecular biological manipulation.

A "vector" is any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. Viral vectors include retrovirus, adeno-associated virus, pox, baculovirus, vaccinia, herpes simplex, Epstein-Barr and adenovirus vectors, as set forth in greater detail below. Non-viral vectors include plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cloning vector" is a replicon, such as plasmid, phage or cosmid, to which another DNA segment may be attached so as to bring about the replication of the attached segment. Cloning vectors may be capable of replication in one cell type, and expression in another ("shuttle vector").

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix.

Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

As used herein, the term "oligonucleotide" refers to a nucleic acid, generally of at least 18 nucleotides, that is hybridizable to a genomic DNA molecule, a cDNA molecule, or an mRNA molecule encoding Akt3. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid encoding Akt3. In another embodiment, oligonucleotides (one or both of which may be labeled) can be used as PCR primers, either for cloning full length or a fragment of Akt3, or to detect the presence of nucleic acids encoding Akt3. In a further embodiment, an oligonucleotide of the invention can form a triple helix with an Akt3 DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

An "antisense nucleic acid" is a sequence of nucleotides that is complementary to the sense sequence. Antisense nucleic acids can be used to down regulate or block the expression of the polypeptide encoded by the sense strand.

Transcriptional and translational control sequences are DNA regulatory sequences, such as promoters, enhancers, terminators, and the like, that provide for the expression of a coding sequence in a host cell. In eukaryotic cells, polyadenylation signals are additional types of control sequences.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin which are responsible for expressing different proteins or even synthetic proteins (a heterologous region). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, promoters, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"Heterologous" DNA refers to DNA not naturally located in the cell, or in a chromosomal site of the cell. Preferably, the heterologous DNA includes a gene foreign to the cell.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A "polypeptide" is a polymeric compound comprised of covalently linked amino acid residues. Amino acids have the following general structure:

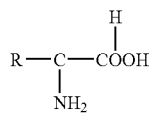

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide which plays a structural or functional role in a living cell.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant of the invention preferably comprises at least about 14 amino acids.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "heterologous protein" refers to a protein not naturally produced in the cell.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

Genes Encoding Akt3 Proteins

The present invention contemplates isolation of a gene encoding a human Akt3 protein or polypeptide of the invention, including a full length, or naturally occurring form of Akt3, and any human Akt3-specific antigenic fragments thereof. As used herein, "Akt3" refers to Akt3 polypeptide, and "akt3" refers to a gene encoding Akt3 polypeptide. For the purpose of the present invention, the term Akt3 denotes any protein or polypeptide capable of inhibiting apoptosis, and which comprises the sequence Cys-Gln-Gln-Ser-Asp-Cys-Gly-Met-Leu-Gly-Asn-Trp-Lys-Lys, or a substantially similar sequence. Preferably, the sequence Cys-Gln-Gln-Ser-Asp-Cys-Gly-Met-Leu-Gly-Asn-Trp-Lys-Lys, or substantially similar sequence, occurs at the C-terminus of the Akt3 protein.

Preferably, the novel Akt3 according to the invention comprises an amino acid sequence as shown in SEQ ID NO: 2. A preferred nucleic acid according to the invention encodes an amino acid sequence as shown in SEQ ID NO: 2. More preferably, the nucleic acid comprises a sequence as depicted in SEQ ID NO: 1.

A first subject of the invention relates to an isolated nucleic acid encoding a novel Akt protein or polypeptide, optionally under the control of regions permitting its expression in mammalian cells. The invention also relates to vectors containing the nucleic acid encoding the Akt protein or polypeptide, and to the use of these nucleic acids or vectors for the preparation of pharmaceutical compositions intended for the surgical and/or therapeutic treatment of the human or animal body. It also relates to any pharmaceutical composition comprising a vector, such as a viral vector, and a nucleic acid as defined above.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A gene encoding Akt3, whether genomic DNA or cDNA, can be isolated from any source, particularly from a human cDNA or genomic library. General methods for obtaining an akt3 gene are well known in the art, as described above (see, e.g., Sambrook et al., 1989, supra).

Accordingly, any animal cell potentially can serve as the nucleic acid source for the molecular cloning of a akt3 gene. The DNA may be obtained by standard procedures known in the art from cloned DNA (e.g., a DNA "library"), and preferably is obtained from a cDNA library prepared from tissues with high level expression of the protein (e.g., heart, pancreas and skeletal muscle cDNA, since these are the cells that evidence high levels of expression of Akt3), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Once the DNA fragments are generated, identification of the specific DNA fragment containing the desired akt3 gene may be accomplished in a number of ways. For example, DNA fragments may be screened by nucleic acid hybridization to a labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. As noted above, the greater the degree of homology, the more stringent hybridization conditions can be used. In a specific embodiment, Northern hybridization conditions are used to identify mRNA splicing variants of an akt3 gene.

Further selection can be carried out on the basis of the properties of the gene, e.g., if the gene encodes a protein product having the isoelectric, electrophoretic, amino acid composition, or partial amino acid sequence of Akt3 protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for Akt3. In a specific embodiment, the expressed protein is recognized by a polyclonal antibody that is generated against an epitope specific for human Akt3, such as within the amino acid sequence Cys-Gln-Gln-Ser-Asp-Cys-Gly-Met-Leu-Gly-Asn-Trp-Lys-Lys.

The present invention also relates to genes (e.g., cDNAs) encoding allelic variants, splicing variants, analogs, and derivatives of Akt3 of the invention, that have the same or homologous functional activity as Akt3, and homologs thereof from other species. The production and use of derivatives and analogs related to Akt3 are within the scope of the present invention. Such variants, analogs, derivatives and homologs should retain the sequence Cys-Gln-Gln-Ser-Asp-Cys-Gly-Met-Leu-Gly-Asn-Trp-Lys-Lys, or a substantially similar sequence. In a specific embodiment, the derivative or analog is functionally active, i.e., capable of exhibiting one or more functional activities associated with a full-length, wild-type Akt3 of the invention.

Akt3 derivatives can be made by altering encoding nucleic acid sequences by substitutions, additions or deletions that provide for functionally equivalent molecules. Preferably, derivatives are made that have enhanced or increased functional activity relative to native Akt3.

Due to the degeneracy of nucleotide coding sequences, other DNA sequences which encode substantially the same amino acid sequence as a akt3 gene, including an amino acid sequence that contains a single amino acid variant, may be used in the practice of the present invention. These include but are not limited to allelic genes, homologous genes from other species, and nucleotide sequences comprising all or portions of akt3 genes which are altered by the substitution of different codons that encode the same amino acid residue within the sequence, thus producing a silent change. Likewise, the Akt3 derivatives of the invention include, but are not limited to, those containing, as a primary amino acid sequence, all or part of the amino acid sequence of a Akt3 protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrpsine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:
  Lys for Arg and vice versa such that a positive charge may be maintained;
  Glu for Asp and vice versa such that a negative charge may be maintained;
  Ser for Thr such that a free —OH can be maintained; and
  Gln for Asn such that a free $CONH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding Akt3 derivatives and analogs of the invention can be produced by various methods known in the art. The manipulations which result in their production can occur at the gene or protein level. For example, the cloned Akt3 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of Akt3, care should be taken to ensure that the modified gene remains within the same translational reading frame as the Akt3 gene, uninterrupted by translational stop signals, in the gene region where the desired activity is encoded.

Additionally, the Akt3-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated Akt3 gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in PCR Technology: Principles and Applications for DNA Amplification, H. Erlich, ed., Stockton Press, Chapter 6, pp. 61-70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, E. coli, bacteriophages such as lambda derivatives, or plasmids such as pBR322 derivatives or pUC plasmid derivatives, e.g., pGEX vectors, pmaI-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E. coli plasmid with sequences form the yeast 2μ plasmid.

Expression of Akt3 Polypeptides

The nucleotide sequence coding for Akt3, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding Akt3 and/or its flanking regions. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant Akt3 protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding Akt3 is cultured in an appropriate cell culture medium under conditions that provide for expression of Akt3 by the cell. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

A nucleic acid encoding an Akt3 polypeptide may be operably linked and controlled by any regulatory region, i.e., promoter/enhancer element known in the art, but these regulatory elements must be functional in the host target tumor selected for expression. The regulatory regions may comprise a promoter region for functional transcription in the host cell, as well as a region situated 3' of the gene of interest, and which specifies a signal for termination of transcription and a polyadenylation site. All these elements constitute an expression cassette.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, such as adenovirus (E1A and MLP), cytomegalovirus, or Rous Sarcoma Virus. In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted.

Some promoters useful for practice of this invention are ubiquitous promoters (e.g., HPRT, vimentin, actin, tubulin), intermediate filament promoters (e.g., desmin, neurofilaments, keratin, GFAP), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, cytomegalovirus (CMV) immediate-early, retroviral LTR, metallothionein, SV-40, adenovirus E1a, and adenovirus major late (MLP) promoters. Tetracycline-regulated transcriptional modulators and CMV promoters are described in WO 96/01313, U.S. Pat. Nos. 5,168,062 and 5,385,839, the contents of which are incorporated herein by reference.

More specifically, expression of Akt3 protein may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315: 115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Expression vectors containing a nucleic acid encoding a Akt3 of the invention can be identified by five general approaches: (a) PCR amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding Akt3 is inserted within the "selection marker" gene sequence of the vector, recombinants containing the Akt3 insert can be identified by the absence of the gene function. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMaI-C2, pET, pGEX (Smith et al., 1988, Gene 67:31-40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PsfI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive Rous Sarcoma Virus Long Terminal Repeat (RSV-LTR) promoter, hygromycin selectable marker; Invitrogen), pCEP4 (BamH1, SfiI, XhoI, NotI, NheI, HindIII, NheI, PvuII, and KpnI cloning site, constitutive human cytomegalovirus (hCMV) immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamH1 cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express Akt3. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. Expression in yeast can produce a biologically active product. Expression in eukaryotic cells can increase the likelihood of "native" folding. Moreover, expression in mammalian cells can provide a tool for reconstituting, or constituting, Akt3 activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Antibodies to Akt3

According to the invention, an Akt3 polypeptide produced recombinantly or by chemical synthesis, and fragments or other derivatives or analogs thereof, including fusion proteins, may be used as an antigen or immunogen to generate antibodies. Preferably, the antibodies specifically bind human Akt3, but do not bind other forms of Akt. More preferably, the antibodies recognize an epitope within a peptide having the sequence Cys-Gln-Gln-Ser-Asp-Cys-Gly-Met-Leu-Gly-Asn-Trp-Lys-Lys, or a substantially similar sequence.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Such antibodies include but are not limited to polyclonal, monoclonal, chimeric, single chain, Fab fragments, and an Fab expression library. The anti-Akt3 antibodies of the invention may be cross reactive, e.g., they may recognize Akt3 from different species. Polyclonal antibodies have greater likelihood of cross reactivity. Alternatively, an antibody of the invention may be specific for a single form of Akt3, such as human Akt3. Preferably, such an antibody is specific for human Akt3.

Various procedures known in the art may be used for the production of polyclonal antibodies. For the production of antibody, various host animals can be immunized by injection with the Akt3 polypeptide, or a derivative (e.g., fragment or fusion protein) thereof, including but not limited to rabbits, mice, rats, sheep, goats, etc. In one embodiment, the Akt3 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the Akt3 polypeptide, or fragment, analog, or derivative thereof, any technique that provides for the production of antibody molecules by continuous cell lines in culture may be used. These include but are not limited to the hybridoma technique originally developed by Kohler and Milstein [*Nature* 256:495-497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals [International Patent Publication No. WO 89/12690, published 28 Dec. 1989]. In fact, according to the invention, techniques developed for the production of "chimeric antibodies" [Morrison et al., *J. Bacteriol.* 159:870 (1984); Neuberger et al., *Nature* 312:604-608 (1984); Takeda et al., *Nature* 314:452-454 (1985)] by splicing the genes from a mouse antibody molecule specific for an Akt3 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain Fv (scFv) antibodies [U.S. Pat. Nos. 5,476,786 and 5,132,405 to Huston; U.S. Pat. No. 4,946,778] can be adapted to produce Akt3 polypeptide-specific single chain antibodies. An additional embodiment of the invention utilizes the techniques described for the construction of Fab expression libraries [Huse et al., *Science* 246: 1275-1281 (1989)] to allow rapid and easy identification of monoclonal Fab fragments with the desired specificity for an Akt3 polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an Akt3 polypeptide, one may assay generated hybridomas for a product which binds to an Akt3 polypeptide fragment containing such epitope. A preferred fragment comprises the sequence Cys-Gln-Gln-Ser-Asp-Cys-Gly-Met-Leu-Gly-Asn-Trp-Lys-Lys. For selection of an antibody specific to an Akt3 polypeptide from a particular species of animal, one can select on the basis of positive binding with Akt3 polypeptide expressed by or isolated from cells of that species of animal. The foregoing antibodies can be used in methods known in the art relating to the localization and activity of the Akt3 polypeptide, e.g., for Western blotting, imaging Akt3 polypeptide in situ, measuring levels thereof in appropriate physiological samples, etc. using any of the detection techniques mentioned above or known in the art.

In a specific embodiment, antibodies that agonize or antagonize the activity of Akt3 polypeptide can be generated. Such antibodies can be tested using the assays described infra for identifying ligands. In particular, such antibodies can be scFv antibodies expressed intracellularly.

Gene Therapy and Transgenic Vectors

Death of cardiac myocytes through apoptosis and necrosis contributes to acute myocardial infarction and heart failure. Human Akt3 inhibits ASK1-induced and hypoxia-induced apoptosis and cell death. Therefore, the present invention includes gene therapy by the administration to a patient of a nucleic acid encoding a human Akt3 protein. In the case of acute myocardial infarction, gene therapy using Akt3 is expected to reduce the quantity of cell death and the final infarct size, thereby resulting in improved post-infarction function, improved quality of life and reduced mortality. In addition, reduced infarct size is expected to reduce the number of patients developing heart failure following infarction. In patients with existing heart failure, reducing the loss of myocytes by gene therapy with Akt-3 is expected to retard the process of ventricular dilation, slow disease progression, improve quality of life and reduce the need for hospitalization.

During acute myocardial infarction the process of ischemia-reperfusion injury results in cell death. Akt-3 inhibits cell death. Therefore, it is expected that Akt3 gene therapy will be an effective treatment for other disease states involving ischemia-reperfusion injury, including, but not limited to, myocardial ischemia reperfusion injury, stroke, liver damage, renal failure, organ transplantation (especially cardiac), and coronary artery bypass grafting. In addition, Akt-3 gene therapy is expected to be an effective treatment for other disease states involving cell death via apoptosis, including, but not limited to, Alzheimer's disease, liver degeneration and osteoarthritis.

The nucleic acids of the invention, where appropriate incorporated in vectors, and the pharmaceutical compositions containing them, may be used for the treatment of many pathologies. They may be used for the transfer and expression of genes in vivo in any type of tissue, especially the heart. The treatment can, moreover, be targeted in accordance with the pathology to be treated (transfer to a particular tissue can, in particular, be determined by the choice of a vector, and expression by the choice of a particular promoter). The nucleic acids or vectors of the invention are advantageously used for the production in humans or animals, in vivo and intracellularly, of proteins capable of acting specifically on various cell functions such as protection from hypoxia-induced cell death, apoptosis, myocardial infarction, necrosis, cell proliferation, synthesis of metabolites, protein synthesis, DNA replication and/or transcription, and the like? The present invention thus makes it possible to treat specifically, locally and effectively cell dysfunctions at the origin of or resulting from different pathologies, and especially involving apoptosis.

As discussed above, a "vector" is any means for the transfer of a nucleic acid according to the invention into a host cell. Preferred vectors are viral vectors, such as retroviruses, herpes viruses, adenoviruses, and adeno-associated viruses. Thus, a gene encoding an Akt3 protein or polypeptide domain fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Expression vectors of the invention can be used, as pointed out above, both to transfect cells for screening or biological testing of modulators of Akt3 activity, or for delivery of a akt3 gene or akt3 antisense gene in vivo or ex vivo for gene therapy, e.g., to increase or decrease the level of Akt3 activity. A vector that expresses an anti-Akt3 scFv can also be introduced using the techniques discussed below.

Viral vectors commonly used for in vivo or ex vivo targeting and therapy procedures are DNA-based vectors and retroviral vectors. Methods for constructing and using viral vectors are known in the art [see, e.g., Miller and Rosman, *BioTechniques* 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Defective viruses, which entirely or almost entirely lack viral genes, are preferred. Defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., *Molec. Cell. Neurosci.* 2:320-330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Strafford-Perricaudet et al. [*J. Clin. Invest* 90:626-630 (1992); see also La Salle et al., *Science* 259:988-990 (1993)]; and a defective adeno-associated virus vector [Samulski et al., *J. Virol.* 61:3096-3101 (1987); Samulski et al., *J. Virol.* 63:3822-3828 (1989); Lebkowski et al., *Mol. Cell. Biol.* 8:3988-3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-$\gamma$ (IFN-$\gamma$), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

Naturally, the invention contemplates delivery of a vector that will express a therapeutically effective amount of Akt3 for gene therapy applications. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Adenovirus Vectors

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-Associated Virus Vectors

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterised. It encompasses approximately 4700 bases and contains an inverted terminal repeat (ITR) region of approximately 145 bases at each end, which serves as an origin of replication for the virus. The remainder of the genome is divided into two essential regions which carry the encapsulation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsulation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a nucleic acid encoding an Akt3 flanked by the AAV ITRs. The invention also relates to a plasmid encompassing a sequence encoding a nucleic acid encoding an Akt3 flanked by two ITRs from an AAV. Such a plasmid can be used as it is for transferring the nucleic acid sequence, with the plasmid, where appropriate, being incorporated into a liposomal vector (pseudo-virus).

Retrovirus Vectors

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, Bio Technology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. The retrovirus genome includes two LTRs, an encapsulation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsulation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm$^{-12}$ cell line (WO89/07150). In addition, the recombinant retroviral vectors can contain modifications within the LTRs for suppressing transcriptional activity as well as extensive encapsulation sequences which may include a part of the gag gene (Bender et al., J. Virol. 61 (1987) 1639). Recombinant retroviral vectors are purified by standard techniques known to those having ordinary skill in the art.

Retroviral vectors can be constructed to function as infections particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Targeted gene delivery is described in International Patent Publication WO 95/28494, published October 1995.

Non-Viral Vectors

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., Proc. Natl. Acad. Sci. U.S.A. 84:7413-7417 (1987); see Mackey, et al., Proc. Natl. Acad. Sci. U.S.A. 85:8027-8031 (1988); Ulmer et al., Science 259:1745-1748 (1993)]. The use of cationic lipids may promote encapsulation of negatively charged nucleic acids, and also promote fusion with negatively charged cell membranes [Felgner and Ringold, Science 337:387-388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid (see U.S. Pat. Nos. 5,693,622, 5,589,466 and 5,580,859). Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963-967 (1992); Wu and Wu, J. Biol. Chem. 263:14621-14624 (1988); Hartmut et al., Canadian Patent Application No. 2,012,311, filed Mar. 15, 1990; Williams et al., Proc. Natl. Acad. Sci. USA 88:2726-2730 (1991)]. Receptor-mediated DNA delivery approaches can also be used [Curiel et al., Hum. Gene Ther. 3:147-154 (1992); Wu and Wu, J. Biol. Chem. 262: 4429-4432 (1987)]. Preferred naked DNA vectors include pCOR plasmids having a conditional origin of replication (see WO97/10343), and minicircle plasmids lacking an origin of replication and a marker gene (see WO96/26270).

Pharmaceutical Compositions and Delivery

The present invention also relates to a pharmaceutical compositions. Such compositions may comprise an Akt protein or polypeptide or a nucleic acid encoding an Akt protein or polypeptide, as defined above, and a pharmaceutically acceptable carrier or vehicle. The compositions of the invention are particularly suitable for formulation of biological material for gene therapy. Thus, in a preferred embodiment, the composition comprises a nucleic acid encoding a human Akt3 protein or polypeptide.

Any vector, viral or non-viral, of the invention will preferably be introduced in vivo in a pharmaceutically acceptable vehicle or carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The pharmaceutical compositions of the invention may be formulated for the purpose of topical, oral, parenteral, intranasal, intravenous, intramuscular, subcutaneous, intraocular, and the like, administration.

Preferably, the pharmaceutical compositions contain pharmaceutically acceptable vehicles for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on addition, as appropriate, of sterilized water or of physiological saline, enable injectable solutions to be formed.

The compositions may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, allow the constitution of injectable solutions.

The preferred sterile injectable preparations can be a solution or suspension in a nontoxic parenterally acceptable solvent or diluent. Examples of pharmaceutically acceptable carriers or vehicles are saline, buffered saline, isotonic saline (e.g., monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The doses of nucleic acids of the invention, either alone or incorporated in a vector, used for administration can be adjusted in accordance with different parameters, and in particular in accordance with the mode of administration used, the pathology in question, the gene to be expressed or the desired treatment period. Generally speaking, in the case of the recombinant viruses according to the invention, these are formulated and administered in the form of doses of between $10^4$ and $10^{14}$ pfu, and preferably $10^6$ to $10^{10}$ pfu. The term pfu (plaque forming unit) corresponds to the infectious power of a solution of virus, and is determined by infection of a suitable cell culture and measurement, generally after 48 hours, of the number of infected cell plaques. The techniques of determination of the pfu titre of a viral solution are well documented in the literature.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The composition of the invention may be introduced parenterally or transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. The administration of the composition may introduced by injection directly into the site to be treated, in particular, into the heart.

The preferred route of administration to the heart is by direct injection into the heart (U.S. Pat. No. 5,693,622). The heart can be imaged using any of the techniques available in the art, such as magnetic resonance imaging or computer-assisted tomography, and the therapeutic composition administered by stereotactic injection, for example. Administration to the heart can also occur through the use of a catheter (U.S. Pat. No. 5,851,521).

In yet another embodiment, a composition comprising a human Akt3 polypeptide, or nucleic acid encoding the polypeptide, can be delivered in a controlled release system. For example, the nucleic acid or polypeptide may be administered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.* 14:201 (1987); Buchwald et al., *Surgery* 88:507 (1980); Saudek et al., N. Engl. J. Med. 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the heart, thus requiring only a fraction of the systemic dose [see, e.g., Goodson, in *Medical Applications of Controlled Release*, supra, vol. 2, pp. 115-138 (1984)]. Other controlled release systems are discussed in the review by Langer [*Science* 249:1527-1533 (1990)].

Thus, the compositions of the invention can be delivered by intravenous, intraarterial, intraperitoneal, intramuscular, or subcutaneous routes of administration. Alternatively, the compositions, properly formulated, can be administered by nasal or oral administration. A constant supply of the biological material can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

An organism in whom administration of a biological material within the scope of the invention is administered is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Screening Assays

Identification and isolation of a gene encoding an Akt3 protein of the invention provides for expression of Akt3 in quantities greater than can be isolated from natural sources, or in indicator cells that are specially engineered to indicate the activity of Akt3 expressed after transfection or transformation of the cells. Accordingly, in addition to rational design of agonists and antagonists based on the structure of Akt3 polypeptide, the present invention contemplates an alternative method for identifying specific ligands of Akt3 using various screening assays known in the art.

Akt3 protects cells from apoptosis. Therefore, agonists of Akt3 which enhance its ability to inhibit apoptosis will be expected to improve its activity during treatment of patients suffering myocardial infarction or ischemia-reperfusion injury. On the other hand, increased cell survival is a factor for tumor development, and, therefore, may contribute to tumor formation and/or progression. Therefore, inhibitors of Akt3 activity are expected to decrease tumor cell survival and result in tumor regression.

Any screening technique known in the art can be used to screen for Akt3 agonists or antagonists. For example, a suitable cell line expressing both human Akt3 and ASK1, such as human embryonic kidney HEK293 cells, can be transfected with a nucleic acid encoding a marker gene, such as β-galactosidase. Cells are then exposed to a test solution comprising an agonist or antagonist, and then stained for β-galactosidase activity. The presence of more β-gal positive cells relative to control cells not exposed to the test solution is an indication of the presence of an Akt3 agonist in the test solution. Conversely, the presence of less β-gal positive cells relative to control cells not exposed to the test solution is an indication of the presence of an Akt3 antagonist in the test solution.

The present invention contemplates screens for small molecule ligands or ligand analogs and mimics, as well as screens for natural ligands that bind to and agonize or antagonize Akt3 in vivo. For example, natural products libraries can be screened using assays of the invention for molecules that agonize or antagonize Akt3 activity.

Knowledge of the primary sequence of Akt3, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386-390 (1990); Cwirla, et al., *Proc. Natl. Acad. Sci.*, 87:6378-6382 (1990); Devlin et al., *Science*, 249:404-406 (1990)], very large libraries can be constructed (106-108 chemical entities). A second approach uses primarily chemical methods, of which the Geysen method [Geysen et al., Molecular Immunology 23:709-715 (1986); Geysen et al. J. Immunologic Method 102: 259-274 (1987)] and the method of Fodor et al. [Science 251:767-773 (1991)] are examples. Furka et al. [14th International Congress of Biochemistry, Volume 5, Abstract FR:013 (1988); Furka, Int. J. Peptide Protein Res. 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700-4 (1993); Ohlmeyer et al., Proc. Natl. Acad. Sci. USA 90:10922-10926 (1993); Lam et al., International Patent Publication No. WO 92/00252; Kocis et al., International Patent Publication No. WO 9428028, each of which is incorporated herein by reference in its entirety], and the like can be used to screen for Akt3 ligands according to the present invention.

The screening can be performed with recombinant cells that express the Akt3, or alternatively, using purified protein, e.g., produced recombinantly, as described above. For example, labeled, soluble Akt3 can be used to screen libraries, as described in the foregoing references.

In one embodiment, Akt3 may be directly labeled. In another embodiment, a labeled secondary reagent may be used to detect binding of an Akt3 to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially Eu 3, to name a few fluorophores), chemiluminescent molecules, radio-isotopes, or magnetic resonance imaging labels. Two color assays may be performed with two or more colored latex beads, or fluorophores that emit at different wavelengths. Labeled may be detected visually or by mechanical/optical means. Mechanical/optical means include fluorescence activated sorting, i.e., analogous to FACS, and micromanipulator removal means.

As exemplified herein, the level of the Akt3 protein can be evaluated by metabolic labeling of the proteins. As the metabolic labeling occurs during in vitro incubation of the tissue biopsy in the presence of culture medium supplemented with [$^{35}$S]-methionine, the level of each of the markers detected may be affected by the in vitro conditions. In addition to metabolic (or biosynthetic) labeling with [$^{35}$S]-methionine, the invention further contemplates labeling with [$^{14}$C]-amino acids and [$^3$H]-amino acids (with the tritium substituted at non-labile positions). Thus, a sample or library of compounds can be directly analyzed after labeling of the proteins therein, e.g., by colorimetric staining using silver, gold, coomassie blue, or amido-schwartz, to mention a few techniques; isotopic labeling, e.g., with [$^{32}$P]-orthophosphate, [125I], [$^{131}$I]; fluorescent or chemiluminescent tags; and immunological detection with labeled antibody or specific binding partner of a marker.

The present invention may be better understood by reference to the following non-limiting Examples, which are provided as exemplary of the invention.

EXAMPLES

General Molecular Biology Techniques

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extraction with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; (2$^{nd}$ Ed. 1989); Ausubel F. M. et al. (eds), "Current Protocols in Molecular Biology", John Wiley & Sons, New York, 1987].

Conventional cloning vehicles include pBR322 and pUC type plasmids and phages of the M13 series. These may be obtained commercially (Bethesda Research Laboratories).

For ligation, DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs)

according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749-8764] using the kit distributed by Amersham.

The enzymatic amplification of DNA fragments by PCR [Polymerase-catalyzed Chain Reaction, Saiki R. K. et al., Science 230 (1985) 1350-1354; Mullis K. B. and Faloona F. A., Meth. Enzym. 155 (1987) 335-350] technique may be performed using a "DNA thermal cycler" (Perkin Elmer Cetus) according to the manufacturer's specifications.

Verification of nucleotide sequences may be performed by the method developed by Sanger et al. [Proc. Natl. Acad. Sci. USA, 74 (1977) 5463-5467] using the kit distributed by Amersham.

Plasmid DNAs may be purified by the Qiagen Plasmid Purification System according to the manufacture's instruction.

Example 1

Cloning of Human Akt3

This example describes the cloning of a nucleic acid encoding Akt3 protein.

Example 1.1 cDNA Library Screening for Akt3

A data base search revealed that one human cDNA clone contains a stretch of human cDNA sequence that is homologous to, but different from human Akt1 and Akt2. To isolate the full length coding sequence of this previously unknown human Akt isoform (herein named human Akt3), a human heart cDNA library was screened with cDNA probe corresponding to the 5'-UTR and coding region for the N-terminal human Akt3.

A human cDNA clone (ID# 479072) was purchased (Genome System Inc.). One fragment of this DNA, which covers part of the 5'-UTR (untranslated region) and part of the 5'-coding sequence of human Akt3, was amplified by polymerase chain reaction (PCR) using the following primers: AKT3-5'UTR-F3 (5' TCC AAA CCC TAA AGC TGA TAT CAC 3'; SEQ ID NO:3) and AKT3-C-R1 (5'CCT GGA TAG CTT CTG TCC ATT C 3'; SEQ ID NO:4). A cDNA probe was labeled with [ax-p32]dCTP using a Random Primer DNA labeling kit (Boerhinger Mannheim) according to the manufacture's instructions. The probe was purified using a Bio-Rad chromatography spin column according to the manufacture's instruction.

Over one million phage clones were initially used for cDNA phage library screening (Clonetech, Cat# HL5027t). Host cells XL1-B were inoculated at 370C overnight in LB media (supplemented with 20 mg/ml tetracycline, 0.2% maltose and 10 mM MgCl2). Phage infection and membrane lifting were carried out as described in Maniatis, 1989. Membranes were denatured, renatured and baked, then pre-hybridized with hybridization solution for 4 hours at 65° C. A denatured form of the p32-labeled probe (heat denatured for 10 minutes) was added to the membranes for overnight hybridization. After hybridization, membranes were serially washed with 2×SSC/0.1% SDS, 1×SSC/0.1% SDS, and 0.5× SSC/0.1% SDS at 65° C. Membranes were air-dried and exposed to Kodak X-ray films. After this primary screening, positive clones were selected for secondary and tertiary screening. Resulting positive phages were purified, and phage DNA converted into plasmid DNA using BM25.8-25 host cells according to the manufacture's (Boerhinger Mannheim) instructions.

Two positive clones were chosen for complete sequencing and further characterization. One of these clones (clone #9) comprises part of the 5'-UTR and the N-terminal coding sequence (aa 1 to 127) of human Akt3. A second clone (clone #1) comprises most of the human Akt3 sequence (aa 15 to the C-terminus) and 3'-UTR. A full length cDNA sequence was formed by the fusion of these two partial sequences. A complete sequence encoding a human Akt3 is shown in SEQ ID NO:1. The corresponding amino acid sequence is shown in SEQ ID NO:2. Alignment of the human Akt3 sequence with the rat Akt3 sequence is shown in FIG. 1A. Alignment of the human Akt3 sequence with those of human Akt1 and Akt2 is shown in FIG. 1B.

Importantly, Akt3 is shorter that Akt1 and Akt2, and there is no significant homology between Akt2 and Akt1 or Akt2 at the C-terminus of the molecules. In particular, the last 14 amino acids in the C-terminal portion of human Akt-3 are different from those present in human Akt1 and Akt2. Significantly, Ser473 in the C-terminus of Akt1 is critical for its regulation (Stokeo et al. 1997, Stephens et al. 1998). Upon growth factor stimulation, the activity of P13K is activated. The product of PI3K, Ptdins(3,4,5)-P binds Akt1, resulting in translocation of Akt1 from the cytoplasm to a location proximal to the inner cytoplasmic membrane, where it is phosphorylated at threonine residue 308 and serine 473 (Downward, 1998). Phosphorylation of these residues are critical for the activation of Akt1. A recently identified protein kinase, PDK1, is responsible for phosphorylation of Thr308. However, the kinase(s) which phosphorylates Ser473 has not yet been identified (Stokeo et al. 1997, Stephens et al. 1998). Human Akt3 lacks Ser473 indicating a different phosphorylation pattern and, therefore, different regulation of Akt3 activity.

Example 1.2

Determination of Akt3 Tissue Distribution by Northern Blot Analysis

To test the expression pattern of Akt3, a multiple human tissue mRNA blot was hybridized with a p32-labeled cDNA probe derived from the specific 5'-UTR of human Akt3. The human multiple tissue mRNA blot was purchased from Clontech. A fragment of human Akt-3 cDNA corresponding to the 5'-UTR was PCR amplified by using the following primers: Akt3-5'UTR-F1 (5'-TTT CGG AGG CTC TAG TTT GGT G-3'; SEQ ID NO:15), and Akt3-5' UTR-R1 (5'-CCC AAC TTG GAG AAA TGG TAC-3'; SEQ ID NO:16). Fifty nanograms of cDNA were labeled using a random primed DNA labeling kit (Boehringer Mannheim) according to the manufacture's instruction. Hybridization was carried out according to the manufacture's instruction using a hybridizing blot with purified and boiled probe at 68° C. for 1 hour (Clontech). After hybridization, the blot was washed two times in solution 1 (2×SSC, 0.05% SDS) at room temperature (20 minutes for each wash). Then the blot was washed in solution 2 (0.1% SSC, 0.1% SDS) at 50° C. for 30 minutes. After washing, the blot was exposed to Kodak X-ray film overnight at −80° C.

Figure 2:
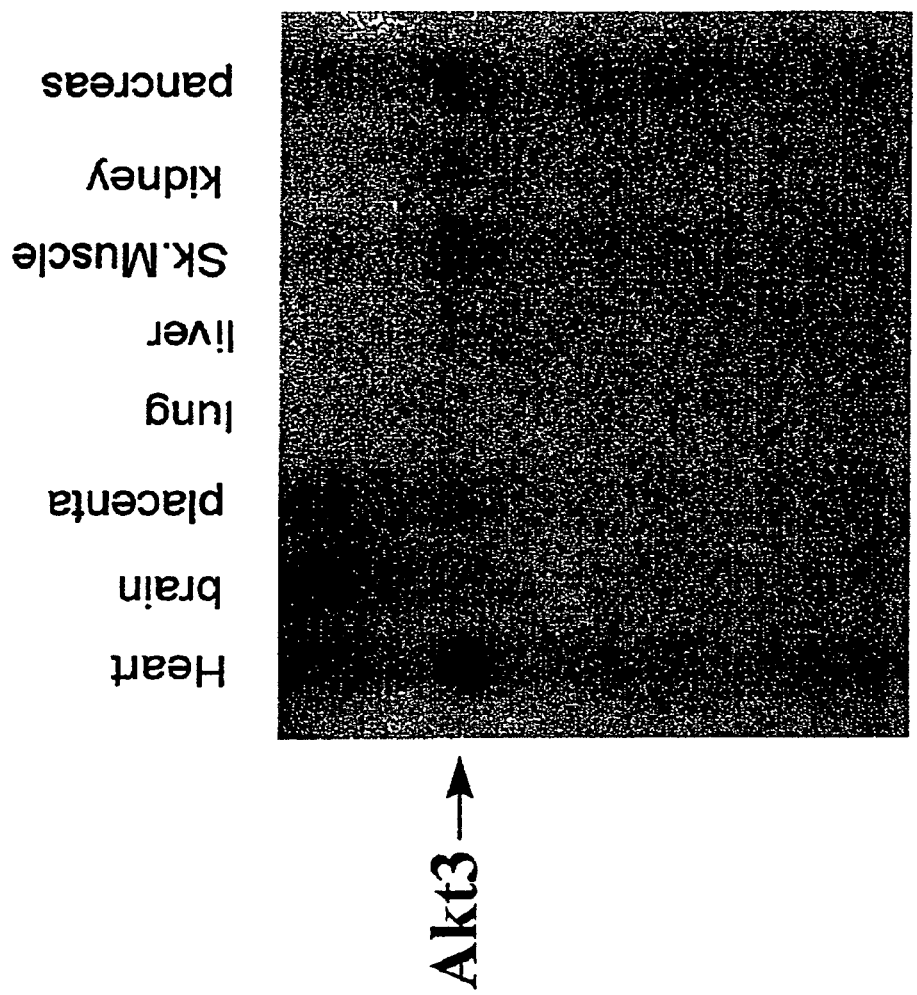
FIG. 2: Tissue distribution pattern of Akt3 mRNA.

The results demonstrate that Akt3 is ubiquitously expressed, with the highest level of expression observed in the heart (FIG. 2).

Example 2

Construction of Akt3 Expression Plasmids

The activity of PI3K is induced upon serum or growth factor stimulation. Activated PI3K convert PI3 into PI3-P, which binds to the AH/PH domain of Akt1, and induces the translocation of Akt1 from the cytoplasm to the cytoplasmic membrane (Downward 1998, Alessi et al. 1996), where Akt is phosphorylated and activated further by PDK1 (Stokoe et al. 1997, Stephens et al. 1998). Akt fused to the myristylation sequence of v-Src (for membrane localization) at the N-terminus leads to membrane localization of the Myr-Akt mutant. This membrane located Akt is constitutively active (Kulik et al, 1997), and inhibits apoptosis induced by various stimuli.

This example describes the construction of an expression plasmid for activated Akt3. First two partial cDNA clones (clone #1 and clone #9, described above) were fused to obtain a full length AKT3 coding sequence. A DNA comprising the human Src myristylation sequence was fused to the N-terminus of the full length Akt3 sequence. An HA-tag sequence was fused to the C-terminus of the full length Akt3 sequence (for detection of expression). The sequence for this chimeric MyrAkt3HA was placed under the control of a CMV promoter. The complete construct is called CMV6-MyrAkt3HA (FIG. 2A).

Example 2.1

CMV6-MyrAktHA

This example describes the construction of plasmids capable of expressing Akt3 and a constitutively active form of human Akt3. A full length Akt3 coding sequence was obtained by PCR amplification of clone #1 using the following primers: hAKT3cl9-PCR5(F): (5'-ATG AGC GAT GTT ACC ATT GTG AAA GAA GGT TGG GTT CAG AAG AGG GGA GAA TAT ATA AAA AAC TGG AGG CCA AG-3'; SEQ ID NO:5), which contains the coding sequence of the first 24 amino acids of Akt3, and hAKT3 cl1-PCR3 (R): (5'-TTA TTT TTT CCA GGT ACC CAG CAT GCC-3'; SEQ ID NO:6).

To make the constitutively active Akt3 form, the coding sequence of full length Akt3 was PCR amplified by using the following primers: MyrAKT3Ha-F1 (5'-GCG CGC GAA TTC CCA CC<u>ATGGGTAGCAACAAGAGCAA GCCCAAGGATGCCAGCCAGCGGCGCCGCA</u> GCA GCG ATG TTA CCA TTG TGA AAG-3'; SEQ ID NO:7), which contains the Kozak sequence (CCACC), the myristylation sequence from human src (underlined) and the first 8 amino acids of human Akt3 (in bold), and MyrAKT3Ha-R (5'-GCG CGC GGG CCC TTA GGC GTA GTC GGG GAC GTC GTA CGG GTA TTT TTT CCA GTT ACC CAG CAT GCC-3'; SEQ ID NO:8), which contains the coding sequence of an HA tag (in bold). The PCR product was digested with EcoR 1/Apa 1 and subcloned into the EcoR 1/Apa 1 sites of pcDNA3.1 producing pcDNA3-Myr-Akt-HA. The coding sequence of MyrAktHA was also PCR amplified and subcloned into the Kpn 1/EcoR 1 sites of the vector CMV6. The primers used for PCR reaction were: CMV6-AKT3cat-F (5'-CGG GGT ACC ACC ATG GGT AGC AAC AAG AGC AAG CCC AAG GAT GCC AGC CAG-3'; SEQ ID NO:9), and CMV6-AKT3cat-R (5'-CCG GAA TTC TTA GGC GTA GTC GGG GAC GTC-3'; SEQ ID NO:10). The plasmid was verified by sequencing.

Example 2.2

Expression of Human AKT3

This example describes the expression of human AKT3 in tissue culture. HEK293 cells and COS-7 cells were maintained in DME media supplemented with 10% fetal bovine serum (FBS). Cells were grown in 37° C., 5% $CO_2$ incubator.

The plasmid CMV6-[MyrAkt3HA] was transiently transfected into HEK293 cells. As a control, HEK293 cells were transfected with the CMV6 vector. One day prior to either transfection, cells were split to a density of $0.2\times10^6$/Cm2. Transfections were carried out using LipofectAmine (Gibco BRL) according to the manufacture's instruction. Briefly, DNA was mixed in DME media (without serum or antibiotics). LipofectAmine was added (DNA:LipofectAmine=1 mg: 4 ml). After brief mixing, the DNA/LipofectAmine mixture was kept at room temperature for 30 minutes. Cells were washed with 1×PBS, and exposed to the DNA/LipofectAmine mixture for 3 hours. After transfection, cells were washed two times with 1×PBS and switched to DMEM-10% FBS media.

Twenty-four hours after transfection, cells were lysed. Lysates were immunoprecipitated with anti-HA antibodies, and the kinase activity of the immunopellets was determined using peptides derived from GSK-3, a downstream target for Akt1 (Cross et al. 1995). In vitro kinase assays for Akt were carried out according to Cross et al (Cross et al, 1995) 24 hours post-transfection. Cells were washed twice in 1×PBS solution, and lysed in lysis buffer (50 mM Tris/HCl, pH 7.4, 1 mM EDTA, 1 mM EGTA, 0.5 mM $Na_3VO_4$, 0.1% β-mercaptoethanol, 1% Triton X-100, 50 mM NaF, 5 mM Sodium pyrophosphate, 10 mM sodium glycerophosphate, 0.5 mM PMSF, 2 ug/ml aprotinin, 2 mg/ml leupeptin, and 1 mM microcystin). Insoluble materials were cleared by centrifugation at 4° C. for 15 minutes. Cell lysates were incubated with polyclonal anti-HA antibodies (BABCO) for 1 hour at 4° C. while on a rotating platform. Protein A-Agarose beads were added to lysates for 1 hour. After immunoprecipitation, pellets were washed three times with washing solution A (lysis buffer supplemented with 0.5M NaCl), three times with washing solution B (50 mM Tris/HCl, pH 7.4, 0.03% Brij35, 0.1 mM EGTA and 0.1% β-mercaptoethanol), and three times with kinase buffer (20 mM MOPS, pH 7.2, 25 mM sodium β-glycerophosphate pH 7.0, 1 mM $Na_3VO_4$, 1 mM DTT). After washing, pellets were resuspended in 40 µl kinase reaction mixture [100 mM ATP, 0.1 mg/ml Crosstide substrate peptide (UBI), 20 mM MgCl2, 10 mM protein kinase A inhibitor/PKI (UBI), and 10 mCi (g-32P)-ATP]. Reactions were carried out at 30° C. for 30 minutes. After completion of the reactions, mixtures were briefly centrifuged, and 30 µl of the supernatant was loaded onto a p81 nitrocellulose paper circle (Gibco BRL). Nitrocellulose papers were washed three times with 180 mM phosphoric acid (10 minutes for each washing), and two times with acetone (2 minutes for each washing). The radioactivity of the paper was monitored by Scintillation Counting Machine. Kinase activity present in CMV6[MyrAkt3HA] transfected samples was 20 times higher than that present in cells transfected with the control vector CMV6, which is similar to the background level observed for this assay (FIG. 2B).

To test the expression of MyrAkt3HA in transfected cells, lysates prepared from transfected cells were subjected to immunobloting with anti-HA antibodies. Cell lysates were prepared as described above, and electrophoresed on SDS polyacrylamide gels. Proteins were transferred to nitrocellulose membranes, which was then treated with blocking solution (1×PBS, 0.2% Tween 20, 5% non-fat dry milk) overnight at 4²C. Membranes were incubated with mouse monoclonal anti-HA antibodies (1:500 dilution in blocking solution) for 3 hours at room temperature. After washing three times with blocking solution (15 minutes each), membranes were incubated with HRP-conjugated rabbit anti-mouse IgG antibodies (1:1000 dilution in blocking solution) for 1 hour at room temperature. After washing three times in blocking solution (10 minutes each) and three times in 1×PBS supplemented with 0.2% Tween 20, membranes were developed in ECL (PIERCE) according to the manufacture's instruction, and exposed to Kodak X-ray film. As shown in FIG. 2C, a strong ~60 KD band (similar to the size of MyrAkt1HA, data not shown) is present in CMV6-[MyrAkt3HA] transfected samples, but not in CMV6 transfected samples (negative control). Taken together, these data demonstrate that transfection with CMV6-[MyrAkt3HA] results in functional Akt activity.

Example 3

Cloning of Human ASK1

This example describes the cloning of a nucleic acid encoding human ASK1 protein. A full length cDNA clone of ASK1 was obtained by screening a human heart cDNA phage library. The probe used for the screening was a fragment of Clone #26237 (Image Consortium) obtained by digestion of pT7T3d with EcoRI/NotI. Library screening, plaque purification and conversion of phage DNA into plasmid DNA were carried out as described above. Clone #4 contained most of the coding sequence of ASK1 (from amino acid 150 to amino acid 1376), and is hereinafter referred to as ASK1-full length. ASK1-full length was PCR amplified by using the following primers: ASK1-Clone#4F(5'-AAG GGC CGC CAG TGT GCT GGA GAG ATG AGC GAT GCC TTC-3'; SEQ ID NO:11), and Ask1-clone#4R (5'-CCC TCT AGA TGC TCA TTC TGC ATT TGA TCC AGC TG-3'; SEQ ID NO:12). The PCR product was purified and subcloned into the BstX1/XbaI sites of the vector pcDNA3-nHA. The correct plasmid, designated pcDNA3-HA-ASK1 (FL), was verified by sequencing. Ichijo et al. (1997) also describes the cloning and the sequence of human ASK1.

Example 4

Inhibition of ASK1-Induced Cell Death

Overexpression of apoptosis stimulating kinase 1 (ASK1) leads to apoptotic cell death (Ichijo et al. 1997). This example demonstrates that expression of human Akt3 inhibits cell death induced by ASK1. A CMV-β-gal plasmid was cotransfected into human embryonic kidney HEK293 cells with the expression plasmid for ASK1 (pcDNA3-HA-ASK1FL), either alone or in combination with the expression plasmid for Akt3 (CMV6-MyrAkt3HA). Two days after transfection, cells were stained for β-galactosidase activity according to the following protocol. Cells were washed three times with 1×PBS ($Mg^{2+}$ and $Ca^{2+}$ free), and fixed in a solution of 3% formaldehyde in PBS for 10 minutes at room temperature. Fixed cells were washed three times with 1×PBS, then stained overnight in a moisture chamber at 37° C. with a solution of 4 mM potassium ferrocyanide, 4 mM potassium ferricyanide, 4 mM $MgCl_2$, 400 mg/ml X-Gal in PBS. The stained cells were washed three times with 1×PBS, and preserved in 70% glycerol. β-gal positive cells were counted under light microscope.

As shown in FIG. 3, transfection with the ASK1 expression plasmid (in the absence of the Akt3 expression plasmid) leads to dramatic decrease in β-gal positive cells. However, cotransfection with the Akt3 expression plasmid significantly inhibits cell death induced by ASK1 as measured by the presence of β-gal positive cells. Taken together, these data demonstrate that activated Akt3 prevents cell death induced by ASK1. The anti-apoptotic activity of Akt3 combined with its high expression in cardiac tissue supports its use for cardioprotection.

ASK1 induces apoptotic cell death in various cell types (Ichijo et al. 1997). However, the molecular mechanism by which ASK1 induces apoptosis is not clear. It has been shown that ectopic expression of ASK1 leads to activation of various stress-activated signaling pathways, such as the MKK4/JNK and MKK6/p38 pathways, and it has been suggested that activation of these pathways mediates ASK1-induced apoptosis (Ichijo et al. 1997). However, addition of a specific inhibitor of p38 has little or no effect on ASK1-induced apoptosis (data not shown), suggesting that ASK1 induces apoptotic cell death independent of p38 kinase activity.

The present results demonstrate that activated Akt3 significantly inhibits ASK1-induced apoptosis, suggesting that Akt3, or one of its downstream target(s), inhibits ASK1-induced apoptotic pathway(s). It has reported that IGF-1 represses JNK activity through a PI3K/Akt-dependent mechanism (Okubo et al. 1998). Akt3 may also act by inhibiting the kinase activity of JNK.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

Aams J M. et al. 1998. The Bcl-2 portein family: arbiters of cell survival. *Science*. Vol281 (5381): 1322-1326.

Alessi D R. et al. 1996. Mechanism of activation of protein kinase B by insulin and IGF-1. *EMBO J*. Vol15(23): 6541-6551.

Baringa M. 1998a. Is apoptosis key in Alzheimer's disease? *Science* Vol281: 1303-1304.

Baringa M. 1998b. Stroke-damaged neurons may commit cellular sucide. *Science* Vol281: 1302-1303.

Chang H Y et al. 1998. Activation of apoptosis signal-regulating kinase (ASK1) by the adapter protein DAXX. *Science*. Vol281 (5384): 1860-1863.

Cross D A. et al. 1995. Inhibition of glycogen synthase kinase-3 by insulin mediated by protein kinase B. *Nature* Vol378(6559):785-789.

Downward J. 1998. Mechanisms and consequences of activation of protein kinase B/Akt. *Curr. Opin. Cell Biol*. Vol10 (2): 262-267

Dudek H. et al. 1997. Regulation of neuronal survival by the serine-threonine protein kinase Akt. *Science* Vol275 (5300): 661-665.

Franke T F. et al. 1995. The protein kinase encoded by the Akt proto-oncogene is a target of PDGF-activated phosphatidylinositol 3-kinase. *Cell* Vol81(5): 727-736.

Franke T F. et al. 1997. PI3K: downstream AKTion blocks apoptosis. *Cell* Vol88(4): 435-437.

Hemmings B A. 1997a. Akt signalling: linking membrane events to life and death decisions. *Science* Vol275(5300): 628-630.

Hemmings B A. 1997b. PtdIns(3.4.5)P3 gets its message across. *Science* Vol277: 534.

Ichijo H. et al. 1997. Induction of apoptosis by ASK1, a mammalian MAPKKK that activates SAPK/JNK and p38 signaling pathways. *Science*. Vol275: 90-94.

Kauffmann-Zeh A. et al. 1997. Suppression of c-Myc-induced apoptosis by Ras signalling through PI(3)K and PKB. *Nature* Vol385(6616): 544-548.

Klippel A. et al. 1997. A specific product of phosphatidylinositol 3-kinase directly activates the protein kinase Akt through its pleckstrin homology domain. *Mol. Cell Biol.* Vol17(1): 338-344.

Konishi H. et al. 1995. Molecular cloning and characterization of a new member of the RAC protein kinase family: association of the pleckstrin homology domain of three types of RAC protein kinase with protein kinase C subspecies and beta gamma subunits of G proteins. *Biochem. Biophys. Res. Comm.* Vol. 216(2): 526-534.

Kulik G. et al. 1997. Antiapoptotic signalling by the insulin-like growth factor I receptor, phosphatidylinositol 3-kinase, and Akt. *Mol. Cell Biol.* Vol 17(3): 1595-1606.

MacLellan W R. et al. 1998. Death by design: programmed cell death in cardiovascular biology and diseases. *Circ. Res.* Vol81(2): 137-144.

Okubo Y. et al. 1998. Insulin-like growth factor-1 inhibits the stress-activated protein kinase/c-Jun N-terminal kinase. *J Biol. Chem.* Vol273: 25961-25966.

Pullen N. et al. 1998. Phosphorylation and activation of p70S6K by PDK1. *Science* Vol279: 707-710.

Sambrook J., Fritsch E F. & Maniatis T. 1989. *Moleucular Cloning* (2nd edition).

Staal S P. 1987. Molecular cloning of the Akt oncogene and its human homologues AKT1 and AKT2: amplification of AKT1 in a primary human gastric adenocarcinoma. *Proc. Natl. Acad. Sci. USA.* Vol84(14): 5034-5037.

Stephens L. et al. 1998. Protein kinase B kinases that mediated phosphatidylinositol 3,4,5-triphosphate-dependent activation of protein kinase B. *Science* Vol279: 710-714.

Stokoe D. et al. 1997. Dual role of phosphatidylinositol-3,4,5-triphosphate in the activation of protein kinase B. *Science* Vol277: 567-570.

Thornberry N A. et al. 1998. Caspases: enemies within. *Science* Vol281: 1312-1316.

The invention claimed is:

1. An in vitro method of inhibiting ASK1-induced cell death, the method comprising: 1) administering to a cell a composition comprising a nucleic acid encoding human Akt3 protein comprising SEQ ID NO: 2 and a human Src myristylation sequence; and 2) expressing said nucleic acid, wherein said human Src myristylation sequence is fused to the N-terminus of said Akt3 protein, wherein expression of Akt3 inhibits ASK1-induced cell death.

2. The method of claim 1, wherein the cell death is cardiac cell death.

3. The method of claim 1, wherein the cell death is cardiac myocyte death.

4. The method of claim 1, wherein the nucleic acid is in a vector.

5. The method of claim 4, wherein the vector is a plasmid.

6. The method of claim 4, wherein the vector is a viral vector.

7. The method of claim 4, wherein the viral vector is selected from the group consisting of retroviruses, adenoviruses, adeno-associated viruses, vaccinia virus and HSV virus.

8. The method of claim 1, wherein the cell death is human embryonic kidney HEK293 cell death.

* * * * *

UNITED STATES PATENT AND TRADEMARK OFFICE
CERTIFICATE OF CORRECTION

| | |
|---|---|
| PATENT NO. | : 7,662,628 B2 |
| APPLICATION NO. | : 11/063691 |
| DATED | : February 16, 2010 |
| INVENTOR(S) | : Guo et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 759 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,662,628 B2
APPLICATION NO. : 11/063691
DATED : February 16, 2010
INVENTOR(S) : Kun Guo et al.

It is certified that error appears in the above-identified patent and that said Letters Patent is hereby corrected as shown below:

On the Title page, Item (56), in column 2, under "Other Publications", line 38, delete "amily" and insert -- Family --, therefor.

On Title page 2, in column 1, under "Other Publications", line 13, delete "PDFG" and insert -- PDGF --, therefor.

On Title page 2, in column 1, under "Other Publications", line 28, delete "vito:" and insert -- vitro: --, therefor .

On Title page 2, in column 1, under "Other Publications", line 47, delete "family" and insert -- family: --, therefor.

On Title page 2, in column 2, under "Other Publications", line 14, delete "programsNucleic" and insert -- programs. Nucleic --, therefor.

On Title page 2, in column 2, under "Other Publications", line 31, delete "Masurs" and insert -- Masure --, therefor.

On Title page 2, in column 2, under "Other Publications", line 41, delete "vol. 8," and insert -- vol. 6, --, therefor.

In column 5, line 22, after "Examples)" insert -- . --.

In column 5, line 44, delete "pcDNA3HA" and insert -- pCDNA3HA --, therefor.

In column 6, line 66, delete "anologs" and insert -- analogs --, therefor.

In column 13, line 12, delete "tyrpsine" and insert -- tyrosine --, therefor.

In column 14, line 9, delete "pmal-c," and insert -- pmaI-c, --, therefor.

In column 17, line 4, delete "pMal-C2," and insert -- pMaI-C2, --, therefor.

In column 17, line 39, delete "(PsfI," and insert -- (PstI, --, therefor.

Signed and Sealed this
Twenty-fifth Day of January, 2011

David J. Kappos
*Director of the United States Patent and Trademark Office*

CERTIFICATE OF CORRECTION (continued)

U.S. Pat. No. 7,662,628 B2

In column 17, line 56, delete "methallothionein" and insert -- metallothionein --, therefor.

In column 18, line 8, delete "HindIII," and insert -- HindII, --, therefor.

In column 30, line 8, delete "fluorescene" and insert -- fluorescein --, therefor.

In column 30, line 32, delete "[125I]," and insert -- [$^{125}$I], --, therefor.

In column 31, line 52, delete "[ax-p32]" and insert -- [α-p32] --, therefor.

In column 31, line 53, delete "Boerhinger" and insert -- Boehringer --, therefor.

In column 31, line 58, delete "Clonetech," and insert -- Clontech, --, therefor.

In column 31, line 59, delete "370C" and insert -- 37°C --, therefor.

In column 32, line 7, delete "Boerhinger" and insert -- Boehringer --, therefor.

In column 33, line 61, delete "pcDNA3.1" and insert -- pCDNA3.1 --, therefor.

In column 33, line 61, delete "pcDNA3" and insert -- pCDNA3 --, therefor.

In column 34, line 67, delete "immunobloting" and insert -- immunoblotting --, therefor.

In column 35, line 5, delete "4$^2$C." and insert -- 4°C. --, therefor.

In column 35, line 43, delete "pcDNA3" and insert -- pCDNA3 --, therefor.

In column 35, line 44, delete "pcDNA3" and insert -- pCDNA3 --, therefor.

In column 35, line 57, delete "(pcDNA3" and insert -- (pCDNA3 --, therefor.

In column 36, line 46, delete "portein" and insert -- protein --, therefor.

In column 36, line 64, after "267" insert -- . --.

In column 38, line 12, delete "Moleucular" and insert -- Molecular --, therefor.

SEQUENCE LISTING

```
<160> NUMBER OF SEQ ID NOS: 17

<210> SEQ ID NO 1
<211> LENGTH: 1570
<212> TYPE: DNA
<213> ORGANISM: Homo sapiens
<220> FEATURE:
<221> NAME/KEY: CDS
<222> LOCATION: (126)..(1523)

<400> SEQUENCE: 1
gtcgacgttg caggctgagt catcactaga gagtgggaag ggcagcagca gcagagaatc      60
caaaccctaa agctgatatc acaaagtacc atttctccaa gttgggggct cagaggggag     120 tcatc atg agc gat gtt acc att gtg aaa gaa ggt tgg gtt cag aag agg     170
      Met Ser Asp Val Thr Ile Val Lys Glu Gly Trp Val Gln Lys Arg
      1               5                  10                  15 gga gaa tat ata aaa aac tgg agg cca aga tac ttc ctt ttg aag aca       218
Gly Glu Tyr Ile Lys Asn Trp Arg Pro Arg Tyr Phe Leu Leu Lys Thr
                20                  25                  30 gat ggc tca ttc ata gga tat aaa gag aaa cct caa gat gtg gat tta       266
Asp Gly Ser Phe Ile Gly Tyr Lys Glu Lys Pro Gln Asp Val Asp Leu
            35                  40                  45 cct tat ccc ctc aac aac ttt tca gtg gca aaa tgc cag tta atg aaa       314
Pro Tyr Pro Leu Asn Asn Phe Ser Val Ala Lys Cys Gln Leu Met Lys
        50                  55                  60 aca gaa cga cca aag cca aac aca ttt ata atc aga tgt ctc cag tgg       362
Thr Glu Arg Pro Lys Pro Asn Thr Phe Ile Ile Arg Cys Leu Gln Trp
    65                  70                  75 act act gtt ata gag aga aca ttt cat gta gat act cca gag gaa agg       410
Thr Thr Val Ile Glu Arg Thr Phe His Val Asp Thr Pro Glu Glu Arg
80                  85                  90                  95 gaa gaa tgg aca gaa gct atc cag gct gta gca gac aga ctg cag agg       458
Glu Glu Trp Thr Glu Ala Ile Gln Ala Val Ala Asp Arg Leu Gln Arg
```

-continued

```
                100                 105                 110
caa gaa gag gag aga atg aat tgt agt cca act tca caa att gat aat      506
Gln Glu Glu Glu Arg Met Asn Cys Ser Pro Thr Ser Gln Ile Asp Asn
            115                 120                 125 ata gga gag gaa gag atg gat gcc tct aca acc cat cat aaa aga aag      554
Ile Gly Glu Glu Glu Met Asp Ala Ser Thr Thr His His Lys Arg Lys
            130                 135                 140 aca atg aat gat ttt gac tat ttg aaa cta cta ggt aaa ggc act ttt      602
Thr Met Asn Asp Phe Asp Tyr Leu Lys Leu Leu Gly Lys Gly Thr Phe
145                 150                 155 ggg aaa gtt att ttg gtt cga gag aag gca agt gga aaa tac tat gct      650
Gly Lys Val Ile Leu Val Arg Glu Lys Ala Ser Gly Lys Tyr Tyr Ala
160                 165                 170                 175 atg aag att ctg aag aaa gaa gtc att att gca aag gat gaa gtg gca      698
Met Lys Ile Leu Lys Lys Glu Val Ile Ile Ala Lys Asp Glu Val Ala
            180                 185                 190 cac act cta act gaa agc aga gta tta aag aac act aga cat ccc ttt      746
His Thr Leu Thr Glu Ser Arg Val Leu Lys Asn Thr Arg His Pro Phe
            195                 200                 205 tta aca tcc ttg aaa tat tcc ttc cag aca aaa gac cgt ttg tgt ttt      794
Leu Thr Ser Leu Lys Tyr Ser Phe Gln Thr Lys Asp Arg Leu Cys Phe
            210                 215                 220 gtg atg gaa tat gtt aat ggg ggc gag ctg ttt ttc cat ttg tcg aga      842
Val Met Glu Tyr Val Asn Gly Gly Glu Leu Phe Phe His Leu Ser Arg
225                 230                 235 gag cgg gtg ttc tct gag gac cgc aca cgt ttc tat ggt gca gaa att      890
Glu Arg Val Phe Ser Glu Asp Arg Thr Arg Phe Tyr Gly Ala Glu Ile
240                 245                 250                 255 gtc tct gcc ttg gac tat cta cat tcc gga aag att gtg tac cgt gat      938
Val Ser Ala Leu Asp Tyr Leu His Ser Gly Lys Ile Val Tyr Arg Asp
            260                 265                 270 ctc aag ttg gag aat cta atg ctg gac aaa gat ggc cac ata aaa att      986
Leu Lys Leu Glu Asn Leu Met Leu Asp Lys Asp Gly His Ile Lys Ile
            275                 280                 285 aca gat ttt gga ctt tgc aaa gaa ggg atc aca gat gca gcc acc atg     1034
Thr Asp Phe Gly Leu Cys Lys Glu Gly Ile Thr Asp Ala Ala Thr Met
            290                 295                 300 aag aca ttc tgt ggc act cca gaa tat ctg gca cca gag gta tta gaa     1082
Lys Thr Phe Cys Gly Thr Pro Glu Tyr Leu Ala Pro Glu Val Leu Glu
            305                 310                 315 gat aat gac tat ggc cga gca gta gac tgg tgg ggc cta ggg gtt gtc     1130
Asp Asn Asp Tyr Gly Arg Ala Val Asp Trp Trp Gly Leu Gly Val Val
320                 325                 330                 335 atg tat gaa atg atg tgt ggg agg tta cct ttc tac aac cag gac cat     1178
Met Tyr Glu Met Met Cys Gly Arg Leu Pro Phe Tyr Asn Gln Asp His
            340                 345                 350 gag aaa ctt ttt gaa tta ata tta atg gaa gac att aaa ttt cct cga     1226
Glu Lys Leu Phe Glu Leu Ile Leu Met Glu Asp Ile Lys Phe Pro Arg
            355                 360                 365 aca ctc tct tca gat gca aaa tca ttg ctt tca ggg ctc ttg ata aag     1274
Thr Leu Ser Ser Asp Ala Lys Ser Leu Leu Ser Gly Leu Leu Ile Lys
            370                 375                 380 gat cca aat aaa cgc ctt ggt gga gga cca gat gat gca aaa gaa att     1322
Asp Pro Asn Lys Arg Leu Gly Gly Gly Pro Asp Asp Ala Lys Glu Ile
385                 390                 395 atg aga cac agt ttc ttc tct gga gta aac tgg caa gat gta tat gat     1370
Met Arg His Ser Phe Phe Ser Gly Val Asn Trp Gln Asp Val Tyr Asp
400                 405                 410                 415 aaa aag ctt gta cct cct ttt aaa cct caa gta aca tct gag aca gat     1418
Lys Lys Leu Val Pro Pro Phe Lys Pro Gln Val Thr Ser Glu Thr Asp
```

```
Lys Lys Leu Val Pro Pro Phe Lys Pro Gln Val Thr Ser Glu Thr Asp
            420                 425                 430 act aga tat ttt gat gaa gaa ttt aca gct cag act att aca ata aca    1466
Thr Arg Tyr Phe Asp Glu Glu Phe Thr Ala Gln Thr Ile Thr Ile Thr
            435                 440                 445 cca cct gaa aaa tgt cag caa tca gat tgt ggc atg ctg ggt aac tgg    1514
Pro Pro Glu Lys Cys Gln Gln Ser Asp Cys Gly Met Leu Gly Asn Trp
            450                 455                 460 aaa aaa taa taaaaagtaa gtttcaatag ctaaaaaaaa aaaaaaaaaa aaaaaa     1570
Lys Lys
    465

<210> SEQ ID NO 2
<211> LENGTH: 465
<212> TYPE: PRT
<213> ORGANISM: Homo sapiens

<400> SEQUENCE: 2

Met Ser Asp Val Thr Ile Val Lys Glu Gly Trp Val Gln Lys Arg Gly
  1               5                  10                  15

Glu Tyr Ile Lys Asn Trp Arg Pro Arg Tyr Phe Leu Leu Lys Thr Asp
             20                  25                  30

Gly Ser Phe Ile Gly Tyr Lys Glu Lys Pro Gln Asp Val Asp Leu Pro
         35                  40                  45

Tyr Pro Leu Asn Asn Phe Ser Val Ala Lys Cys Gln Leu Met Lys Thr
     50                  55                  60

Glu Arg Pro Lys Pro Asn Thr Phe Ile Ile Arg Cys Leu Gln Trp Thr
 65                  70                  75                  80

Thr Val Ile Glu Arg Thr Phe His Val Asp Thr Pro Glu Glu Arg Glu
                 85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
    290                 295                 300
```

```
Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
            325                 330                 335

Tyr Glu Met Met Cys Gly Arg Leu Pro Phe Tyr Asn Gln Asp His Glu
                340                 345                 350

Lys Leu Phe Glu Leu Ile Leu Met Glu Asp Ile Lys Phe Pro Arg Thr
            355                 360                 365

Leu Ser Ser Asp Ala Lys Ser Leu Leu Ser Gly Leu Leu Ile Lys Asp
    370                 375                 380

Pro Asn Lys Arg Leu Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
            435                 440                 445

Pro Glu Lys Cys Gln Gln Ser Asp Cys Gly Met Leu Gly Asn Trp Lys
    450                 455                 460

Lys
465

<210> SEQ ID NO 3
<211> LENGTH: 24
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 3
tccaaaccct aaagctgata tcac                                          24

<210> SEQ ID NO 4
<211> LENGTH: 22
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 4
cctggatagc ttctgtccat tc                                            22

<210> SEQ ID NO 5
<211> LENGTH: 74
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 5
atgagcgatg ttaccattgt gaaagaaggt tgggttcaga agaggggaga atatataaaa    60
aactggaggc caag                                                     74

<210> SEQ ID NO 6
<211> LENGTH: 27
<212> TYPE: DNA
```

<213> ORGANISM: Artificial Sequence
<220> FEATURE:
<220> FEATURE:
<223> OTHER INFORMATION: Description of Artificial Sequence: PCR Primer

<400> SEQUENCE: 6
ttattttttc caggtaccca gcatgcc                                              27

<210> SEQ ID NO 7
<211> LENGTH: 90
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 7
gcgcgcgaat tcccaccatg ggtagcaaca agagcaagcc caaggatgcc agccagcggc          60
gccgcagcag cgatgttacc attgtgaaag                                           90

<210> SEQ ID NO 8
<211> LENGTH: 66
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 8
gcgcgcgggc ccttaggcgt agtcggggac gtcgtacggg tattttttcc agttacccag          60
catgcc                                                                    66

<210> SEQ ID NO 9
<211> LENGTH: 51
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 9
cggggtacca ccatgggtag caacaagagc aagcccaagg atgccagcca g                   51

<210> SEQ ID NO 10
<211> LENGTH: 30
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 10
ccggaattct taggcgtagt cggggacgtc                                           30

<210> SEQ ID NO 11
<211> LENGTH: 39
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 11
aagggccgcc agtgtgctgg agagatgagc gatgccttc                                 39

<210> SEQ ID NO 12
<211> LENGTH: 35
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 12
ccctctagat gctcattctg catttgatcc agctg                    35

<210> SEQ ID NO 13
<211> LENGTH: 480
<212> TYPE: PRT
<213> ORGANISM: Homo sapiens
<220> FEATURE:

<400> SEQUENCE: 13

```
Met Asn Glu Val Ser Val Ile Lys Glu Gly Trp Leu His Lys Arg Gly
  1               5                  10                  15

Glu Tyr Ile Lys Thr Trp Arg Pro Arg Tyr Phe Leu Leu Lys Ser Asp
             20                  25                  30

Gly Ser Phe Ile Gly Tyr Lys Glu Arg Pro Glu Ala Pro Asp Gln Thr
         35                  40                  45

Leu Pro Pro Leu Asn Asn Phe Ser Val Ala Glu Cys Gln Leu Met Lys
     50                  55                  60

Thr Glu Arg Pro Arg Pro Asn Thr Phe Val Ile Arg Cys Leu Gln Trp
 65                  70                  75                  80

Thr Thr Val Ile Glu Arg Thr Phe His Val Asp Ser Pro Asp Glu Arg
                 85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
    290                 295                 300

Ala Thr Met Lys Thr Phe Cys Gly Thr Pro Glu Tyr Leu Ala Pro Glu
```

-continued

```
                305                 310                 315                 320
Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

<210> SEQ ID NO 14
<211> LENGTH: 480
<212> TYPE: PRT
<213> ORGANISM: Homo sapiens

<400> SEQUENCE: 14

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205
```

-continued

```
Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Ser Thr Ala
465                 470                 475                 480

<210> SEQ ID NO 15
<211> LENGTH: 22
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 15
tttcggaggc tctagtttgg tg                                          22

<210> SEQ ID NO 16
<211> LENGTH: 21
<212> TYPE: DNA
<213> ORGANISM: Artificial Sequence
<220> FEATURE:
<220> FEATURE:
<223> OTHER INFORMATION: Description of Artificial Sequence: PCR Primer

<400> SEQUENCE: 16
cccaacttgg agaaatggta c                                           21

<210> SEQ ID NO 17
```

<211> LENGTH: 454
<212> TYPE: PRT
<213> ORGANISM: Artificial Sequence
<220> FEATURE:
<223> OTHER INFORMATION: Description of Artificial Sequence: PCR Primer

<400> SEQUENCE: 17

```
Met Ser Asp Val Thr Ile Val Lys Glu Asp Trp Val Gln Lys Arg Gly
  1               5                  10                  15

Glu Tyr Ile Lys Asn Trp Arg Pro Arg Tyr Phe Leu Leu Lys Thr Asp
             20                  25                  30

Gly Ser Phe Ile Gly Tyr Lys Glu Lys Pro Gln Asp Val Asp Leu Pro
         35                  40                  45

Tyr Pro Leu Asn Asn Phe Ser Val Ala Lys Cys Gln Leu Met Lys Thr
     50                  55                  60

Glu Arg Pro Lys Pro Asn Thr Phe Ile Ile Arg Cys Leu Gln Trp Thr
 65                  70                  75                  80

Thr Val Ile Glu Arg Thr Phe His Val Asp Thr Pro Glu Glu Arg Glu
             85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
    290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
    370                 375                 380
```

-continued

```
Pro Asn Lys Arg Leu Gly Gly Gly Pro Asp Asp Pro Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Cys Pro Leu
    450
```